United States Patent
Greenberg et al.

(10) Patent No.: US 7,105,020 B2
(45) Date of Patent: Sep. 12, 2006

(54) BRANCHED VESSEL ENDOLUMINAL DEVICE

(75) Inventors: Roy K. Greenberg, Bratenahl, OH (US); Karl West, Geneva, OH (US); James Foster, Independence, OH (US); Davorin Skender, Willoughby Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/756,803

(22) Filed: Jan. 13, 2004

(65) Prior Publication Data

US 2004/0193254 A1    Sep. 30, 2004

Related U.S. Application Data

(60) Provisional application No. 60/439,923, filed on Jan. 14, 2003, provisional application No. 60/478,107, filed on Jun. 11, 2003, provisional application No. 60/510,636, filed on Oct. 10, 2003.

(51) Int. Cl.
*A61F 2/06*    (2006.01)

(52) U.S. Cl. ............................ 623/1.35; 606/153

(58) Field of Classification Search ...... 623/1.11–1.35, 623/23.7; 606/153
See application file for complete search history.

(56) References Cited

U.S. PATENT DOCUMENTS

| | | | |
|---|---|---|---|
| 4,592,754 A * | 6/1986 | Gupte et al. ............... | 623/1.25 |
| 4,762,130 A * | 8/1988 | Fogarty et al. ............. | 606/159 |
| 4,902,508 A | 2/1990 | Badylak et al. | |
| 5,129,910 A * | 7/1992 | Phan et al. ................. | 606/127 |
| 5,197,976 A | 3/1993 | Herweck et al. | |
| 5,413,601 A * | 5/1995 | Keshelava ............... | 623/23.69 |
| 5,522,880 A | 6/1996 | Barone et al. | |
| 5,562,724 A | 10/1996 | Vorwerk et al. | |
| 5,571,173 A | 11/1996 | Parodi | |
| 5,578,071 A | 11/1996 | Parodi | |
| 5,591,229 A | 1/1997 | Parodi | |
| 5,617,878 A | 4/1997 | Taheri | |
| 5,653,743 A | 8/1997 | Martin | |
| 5,693,084 A | 12/1997 | Chuter | |
| 5,733,337 A | 3/1998 | Carr, Jr. et al. | |
| 5,824,040 A | 10/1998 | Cox et al. | |
| 5,921,995 A | 7/1999 | Kleshinski | |
| 5,984,955 A | 11/1999 | Wisselink | |
| 6,030,414 A | 2/2000 | Taheri | |
| 6,039,754 A * | 3/2000 | Caro ......................... | 623/1.35 |
| 6,059,824 A | 5/2000 | Taheri | |
| 6,077,296 A | 6/2000 | Shokoohi et al. | |
| 6,093,203 A | 7/2000 | Uflacker | |
| 6,099,558 A | 8/2000 | White et al. | |
| 6,152,956 A | 11/2000 | Pierce | |
| RE37,107 E * | 3/2001 | Wells-Roth ............... | 606/155 |
| 6,210,429 B1 | 4/2001 | Vardi et al. | |

(Continued)

FOREIGN PATENT DOCUMENTS

EP    0 461 791 B1    6/1991

(Continued)

*Primary Examiner*—Suzette J-J Gherbi
(74) *Attorney, Agent, or Firm*—Brinks Hofer Gilson & Lione

(57) ABSTRACT

An endoluminal prosthesis comprises a prosthetic trunk comprising a trunk lumen extending therethrough, a wall, and an anastomosis in the wall, wherein the prosthetic trunk has a circumference. The endoluminal prosthesis further comprises a prosthetic branch comprising a branch lumen extending therethrough. The branch lumen is in fluid communication with the trunk lumen through the anastomosis. The prosthetic branch is disposed longitudinally along and circumferentially about the prosthetic trunk.

32 Claims, 16 Drawing Sheets

U.S. PATENT DOCUMENTS

| | | | |
|---|---|---|---|
| 6,221,090 B1 | 4/2001 | Wilson | |
| 6,290,731 B1 | 9/2001 | Solovay et al. | |
| 6,325,819 B1 | 12/2001 | Pavenik et al. | |
| 6,325,826 B1 | 12/2001 | Vardi et al. | |
| 6,334,869 B1 | 1/2002 | Leonhardt et al. | |
| 6,409,756 B1 | 6/2002 | Murphy | |
| 6,409,757 B1 | 6/2002 | Trout, III et al. | |
| 6,482,227 B1 | 11/2002 | Solovay | |
| 6,517,574 B1 | 2/2003 | Chuter | |
| 6,554,856 B1 * | 4/2003 | Doorly et al. | 623/1.15 |
| 6,582,394 B1 | 6/2003 | Reiss et al. | |
| 6,585,758 B1 | 7/2003 | Chouinard et al. | |
| 6,599,302 B1 * | 7/2003 | Houser et al. | 606/153 |
| 6,652,567 B1 | 11/2003 | Deaton | |
| 6,663,667 B1 | 12/2003 | Dehdashtian et al. | |
| 6,669,720 B1 | 12/2003 | Pierce | |
| 6,706,062 B1 | 3/2004 | Vardi et al. | |
| 6,723,116 B1 | 4/2004 | Taheri | |
| 6,733,522 B1 | 5/2004 | Schmitt et al. | |
| 6,733,523 B1 | 5/2004 | Shaolian et al. | |
| 6,767,358 B1 | 7/2004 | Leonhardt et al. | |
| 6,773,457 B1 | 8/2004 | Ivancev et al. | |
| 2001/0012962 A1 | 8/2001 | Schmitt et al. | |
| 2001/0027338 A1 | 10/2001 | Greenberg | |
| 2001/0037142 A1 | 11/2001 | Stelter et al. | |
| 2002/0052648 A1 | 5/2002 | McGuckin, Jr. et al. | |
| 2002/0058984 A1 | 5/2002 | Butaric et al. | |
| 2002/0058986 A1 | 5/2002 | Landau et al. | |
| 2002/0058987 A1 | 5/2002 | Butaric et al. | |
| 2002/0058991 A1 | 5/2002 | Schmitt | |
| 2002/0058993 A1 | 5/2002 | Landau et al. | |
| 2002/0082684 A1 | 6/2002 | Mishaly | |
| 2002/0099441 A1 | 7/2002 | Dehdashtian | |
| 2002/0111674 A1 | 8/2002 | Chouinard et al. | |
| 2002/0120327 A1 | 8/2002 | Cox et al. | |
| 2002/0143383 A1 | 10/2002 | Parodi | |
| 2002/0144696 A1 | 10/2002 | Sharkawy et al. | |
| 2002/0151957 A1 | 10/2002 | Kerr | |
| 2002/0156517 A1 | 10/2002 | Peroe | |
| 2002/0156522 A1 | 10/2002 | Ivancev et al. | |
| 2002/0173840 A1 | 11/2002 | Brucker et al. | |
| 2002/0193872 A1 | 12/2002 | Trout, III et al. | |
| 2002/0198585 A1 | 12/2002 | Wisselink | |
| 2003/0009212 A1 | 1/2003 | Kerr | |
| 2003/0033005 A1 | 2/2003 | Hoer et al. | |
| 2003/0074050 A1 | 4/2003 | Kerr | |
| 2003/0093145 A1 | 5/2003 | Lawrence-Brown et al. | |
| 2003/0120333 A1 | 6/2003 | Ouriel et al. | |
| 2003/0130720 A1 | 7/2003 | DePalma et al. | |
| 2003/0130724 A1 | 7/2003 | De Palma et al. | |
| 2003/0195614 A1 | 10/2003 | Ryan et al. | |
| 2003/0199967 A1 | 10/2003 | Hartley et al. | |
| 2003/0199973 A1 | 10/2003 | Chuter et al. | |
| 2003/0204242 A1 | 10/2003 | Zarins et al. | |
| 2003/0220682 A1 | 11/2003 | Kujawski | |
| 2003/0225453 A1 | 12/2003 | Murch | |
| 2004/0034406 A1 | 2/2004 | Thramann | |
| 2004/0044396 A1 | 3/2004 | Clerc et al. | |
| 2004/0059406 A1 | 3/2004 | Cully et al. | |
| 2004/0073288 A1 | 4/2004 | Kerr | |
| 2004/0093078 A1 | 5/2004 | Moll et al. | |
| 2004/0106972 A1 | 6/2004 | Deaton | |
| 2004/0133266 A1 | 7/2004 | Clerc et al. | |
| 2004/0138737 A1 | 7/2004 | Davidons et al. | |
| 2004/0167307 A1 | 8/2004 | Frantzen | |

FOREIGN PATENT DOCUMENTS

| | | |
|---|---|---|
| EP | 0 646 365 B1 | 9/1994 |
| EP | 0 903 118 A2 | 9/1994 |
| JP | 404231954 A | 8/1992 |
| JP | 407008512 A | 1/1995 |
| WO | WO 95/16406 | 6/1995 |
| WO | WO 95/21592 A | 8/1995 |
| WO | WO 99/13808 A | 3/1999 |
| WO | WO 99/48441 A | 9/1999 |
| WO | WO 02/067815 A1 | 9/2002 |
| WO | WO 03/065933 A1 | 8/2003 |
| WO | WO 03/082153 A2 | 10/2003 |

* cited by examiner

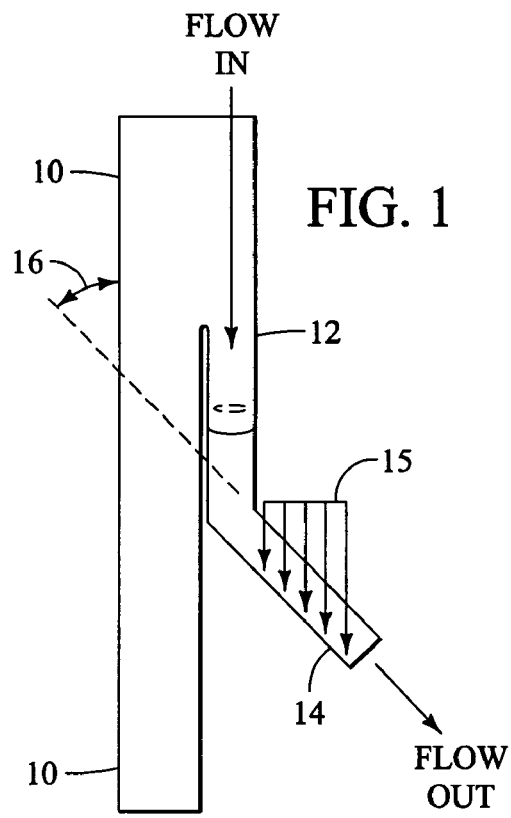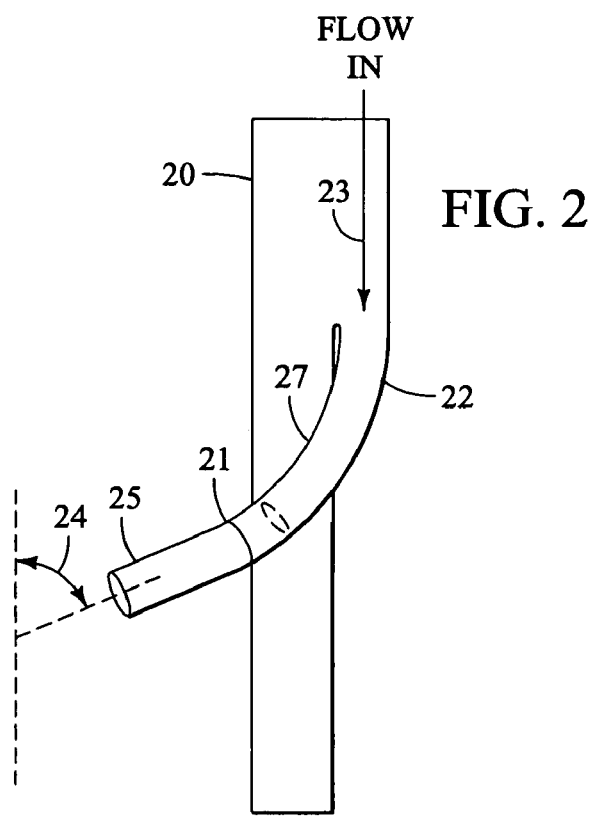

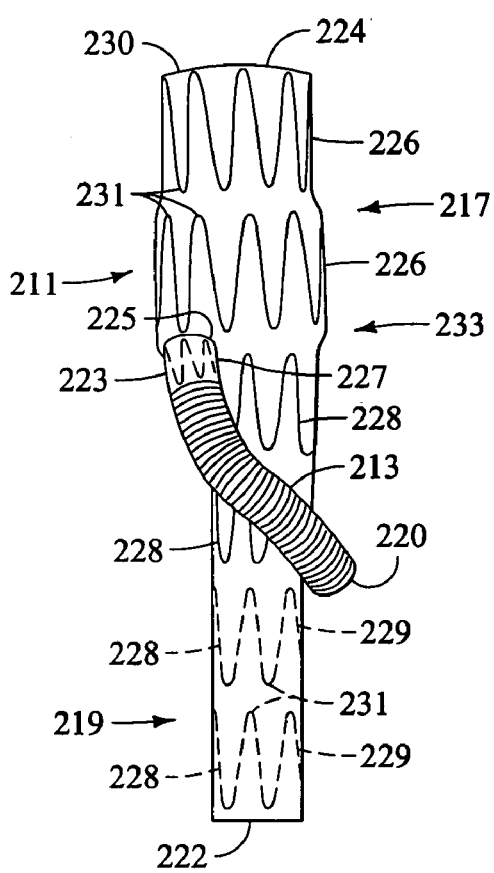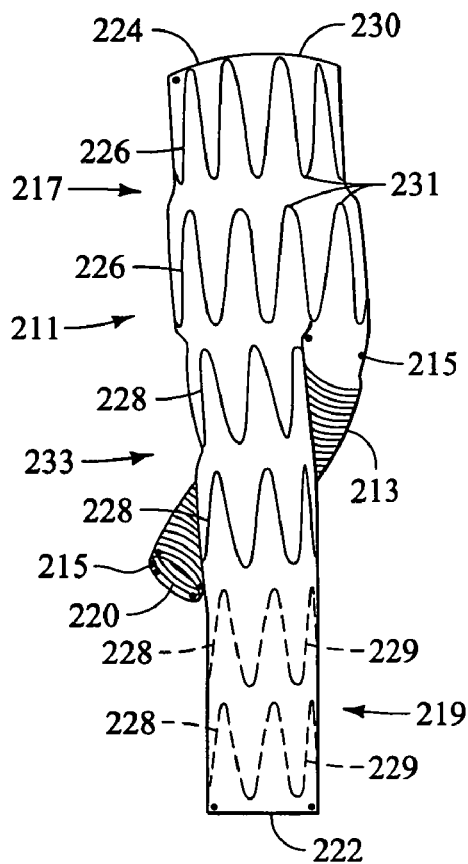
FIG. 11a
FIG. 11b
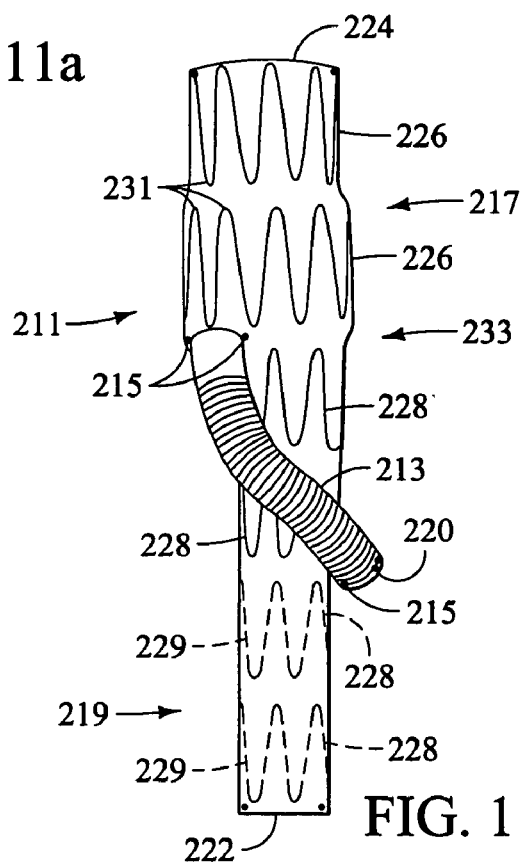
FIG. 11c

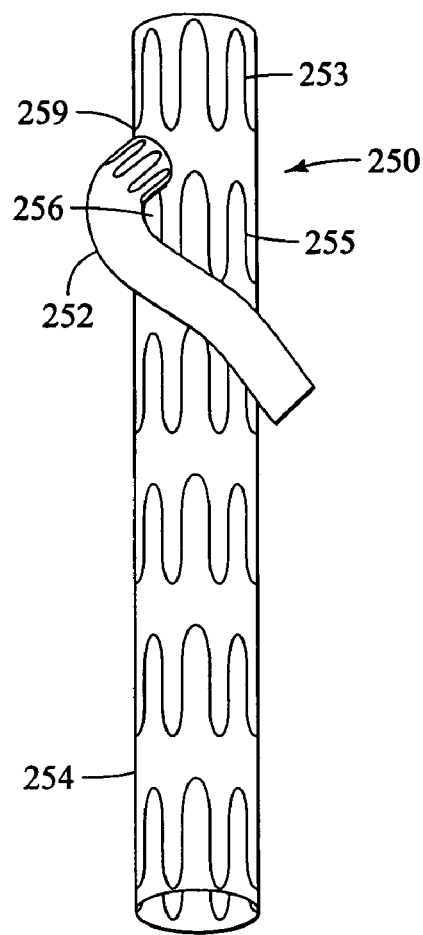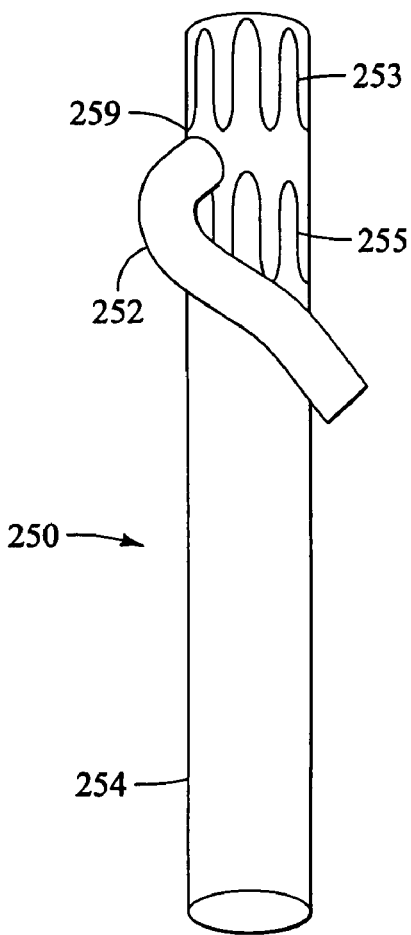
FIG. 12a
FIG. 12b
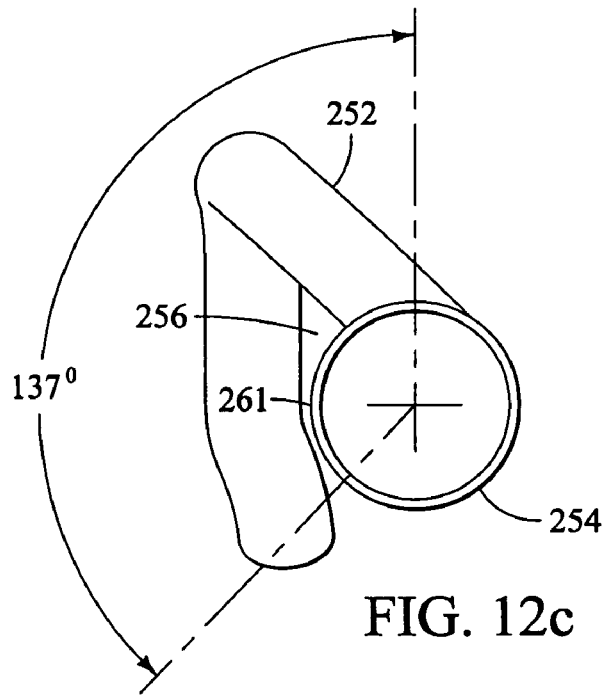
FIG. 12c

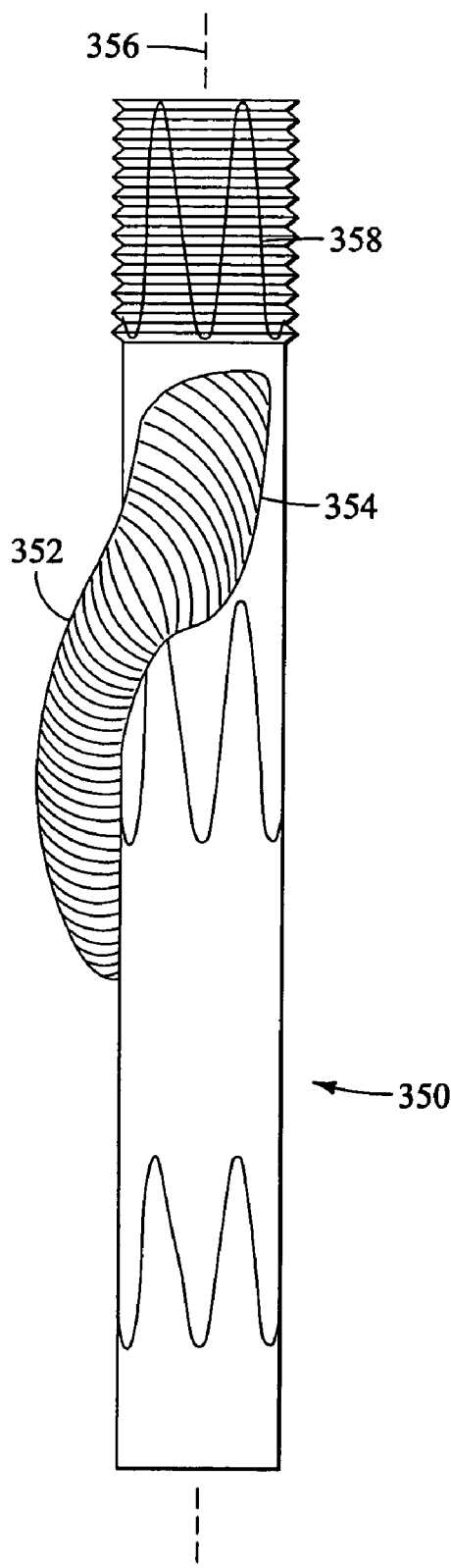 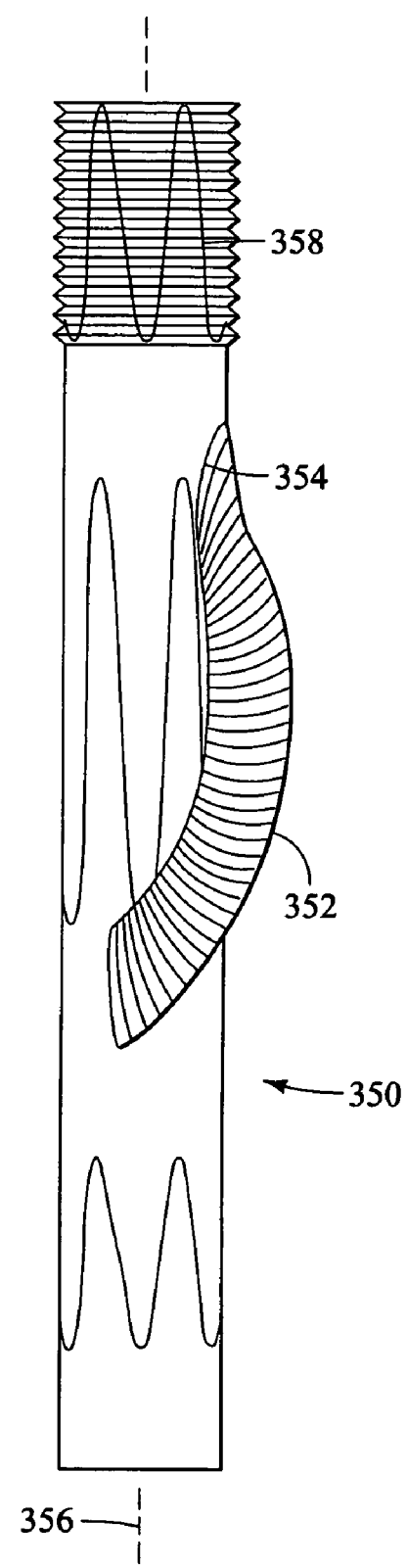
FIG. 14a
FIG. 14b

BRANCHED VESSEL ENDOLUMINAL DEVICE

RELATED APPLICATIONS

This application claims the benefit of U.S. Provisional Application No. 60/439,923, filed Jan. 14, 2003; U.S. Provisional Application No. 60/478,107, filed Jun. 11, 2003; and U.S. Provisional Application No. 60/510,636, filed Oct. 10, 2003, the entire disclosures of which are hereby incorporated by reference.

TECHNICAL FIELD

This invention relates to prostheses for implantation within the human or animal body for the repair of damaged vessels, ducts or other physiological passageways.

BACKGROUND

Throughout this specification, when discussing the application of this invention to the aorta or other blood vessels, the term "distal" with respect to a prosthesis is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal or ruptured vessels involves the use of an endoluminal prosthesis to provide some or all of the functionality of the original, healthy vessel and/or preserve any remaining vascular integrity by replacing a length of the existing vessel wall that spans the site of vessel failure.

It is preferable that these prostheses seal off the failed portion of the vessel. For weakened or aneurysmal vessels, even a small leak in the prosthesis may lead to the pressurization of or flow in the treated vessel, which aggravates the condition the prosthesis was intended to treat. A prosthesis of this type can, for example, treat aneurysms of the abdominal aortic, iliac, or branch vessels such as the renal arteries.

An endoluminal prosthesis can be of a unitary construction, or be comprised of multiple prosthetic modules. A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Modular systems are typically assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the friction forces at the overlap region and enhanced by the radial force exerted by the internal prosthetic module on the external prosthetic modules where the two overlap. The fit may be further enhanced by stents fixed to the modules at the overlap region.

A length of a vessel which may be treated by these prostheses may have one or more branch vessels, i.e. vessels anastomosed to the main vessel. The celiac, superior mesenteric, left common carotid and renal arteries, for example, are branch vessels of the aorta; the hypogastric artery is a branch vessel of the common iliac artery. If these branch vessels are blocked by the prosthesis, the original blood circulation is impeded, and the patient can suffer. If, for example, the celiac artery is blocked by the prosthesis, the patient can experience abdominal pain, weight loss, nausea, bloating and loose stools associated with mesenteric ischemia. The blockage of any branch vessel is usually associated with unpleasant or even life-threatening symptoms.

When treating a vessel with an endoluminal prosthesis, it is therefore preferable to preserve the original circulation by providing a prosthetic branch that extends from the prosthesis to a branch vessel so that the blood flow into the branch vessel is not impeded. For example, the aortic section of the ZENITH® abdominal aortic prosthesis (Cook, Inc., Bloomington, Ind.), described below, can be designed to extend above the renal arteries and to have prosthetic branches that extend into the renal arteries. Alternatively, the iliac branches of the ZENITH® device can be designed to extend into the corresponding hypogastric arteries. Branch extension prosthetic modules ("branch extensions") can form a tromboning connection to the prosthetic branch to complete the prosthesis. Furthermore, some aneurysms extend into the branch vessels. Deploying prosthetic branches and branch extensions into these vessels may help prevent expansion and/or rupture of these aneurysms. High morbidity and mortality rates are associated with these aneurysms.

Typically, existing prosthetic branches have a straight y- or t-shaped connection to the main endoluminal graft. Examples of such prosthetic branches and their associated branch extensions are shown in U.S. Pat. Nos. 6,520,988 and 6,579,309. Some of these branch extensions and their associated prosthetic branches may dislocate, kink and/or cause poor hemodynamics. These problems can lead to thrombogenesis and endoleaks at the interconnection of the prosthetic branch and branch extension.

BRIEF SUMMARY

In one aspect of the invention, there is an endoluminal prosthesis that comprises a prosthetic trunk comprising a trunk lumen extending therethrough, a wall, and an anastomosis in the wall, wherein the prosthetic trunk has a circumference. The endoluminal prosthesis further comprises a prosthetic branch comprising a branch lumen extending therethrough. The branch lumen is in fluid communication with the trunk lumen through the anastomosis. The prosthetic branch is disposed longitudinally along and circumferentially about the prosthetic trunk.

In an embodiment of the prosthesis, the prosthetic branch may extend around the prosthetic trunk at least about one-fourth, at least about one-half or at least about two-thirds the circumference of the prosthetic trunk; the prosthetic branch may extend more than about 10 mm, more than about 30 mm or more than about 50 mm along the prosthetic trunk. The prosthetic branch may be connected at one or more points distally or proximally to the anastomosis. The branch lumen may be inside or outside the prosthetic trunk. A proximal ostium of the prosthetic branch may be infundibular and/or larger than the distal ostium of the prosthetic branch. The distal ostium may be beveled.

An embodiment of this invention may further comprise a second prosthetic branch having a second branch lumen extending therethrough. The second branch lumen is in fluid communication with the trunk lumen through the anastomosis and the second prosthetic branch is disposed longitudinally and circumferentially about the prosthetic trunk. An embodiment of the prosthesis may further comprise a branch extension connected to and in fluid communication with the prosthetic branch.

In an embodiment of the prosthesis, the prosthetic branch may have an angle of access that is greater than 20° or greater than 60°; it may be skewed between about 40° and about 60° or between about 0° and about 40°; it may have an angle of incidence that is between about 20° and about 60° or between about 35° and about 50°.

An embodiment of the prosthesis may be deployed so that the prosthetic trunk is placed at least partially in the abdominal aorta. A prosthetic branch of such a prosthesis may shunt blood flow to a celiac, superior mesenteric, left subclavian, common carotid, innominate, a first renal artery, first and second renal arteries, or any suitable combination of the above listed branch vessels.

An embodiment of the prosthesis may also be deployed so that the prosthetic trunk is placed at least partially in the common iliac. A prosthetic branch of such a prosthesis may shunt blood flow to a hypogastric artery.

An embodiment of the prosthesis may also be deployed so that the prosthetic trunk is placed at least partially in the thoracic aorta. A prosthetic branch of such a prosthesis may shunt blood flow to the innominate, left common carotid or left subclavian artery.

In another aspect of the invention, there is a method of connecting modules of an endoluminal prosthesis that comprises providing a prosthetic trunk, providing a prosthetic branch having proximal and distal ends, anastomosing the proximal end of the prosthetic branch to the prosthetic trunk, positioning the prosthetic branch and attaching the prosthetic branch to the prosthetic trunk so as to provide a helical fluid passage. The method may further comprise attaching the prosthetic branch at a single point on the prosthetic trunk or at multiple points on the prosthetic trunk. The method may also further comprise beveling the distal end of the prosthetic branch. Anastomosing the proximal end of the prosthetic branch to the prosthetic trunk may comprise making a substantially longitudinal cut in the proximal end of the prosthetic branch, splaying the proximal end and attaching a perimeter of the proximal end to the prosthetic trunk.

In yet another aspect of the invention, there is an endoluminal prosthesis that comprises a trunk lumen and a branch lumen. The branch lumen is positioned substantially helically with respect to a longitudinal axis of the trunk lumen. The prosthesis further comprises an anastomosis through which the trunk lumen and the branch lumen are in fluid communication. The branch lumen and the trunk lumen may be in fluid communication through a peripheral anastomosis or a contralateral anastomosis. The branch lumen may originate within the trunk lumen.

In yet another aspect of the invention, there is a method of increasing the angle of access for an endoluminal prosthesis that comprises providing a prosthetic trunk comprising a trunk lumen extending therethrough, a wall and an anastomosis in the wall, and providing a prosthetic branch having a branch lumen extending therethrough. The branch lumen is in fluid communication with the trunk lumen through the anastomosis and disposed longitudinally and circumferentially about the trunk lumen.

BRIEF DESCRIPTION OF THE DRAWINGS

FIG. 1 shows a schematic anterior view of an endoluminal prosthesis with a y-shaped prosthetic branch;

FIG. 2 shows a schematic anterior view of an endoluminal prosthesis with a helical prosthetic branch;

FIG. 3b shows another side view of the embodiment of FIG. 3a;

FIG. 4b shows a schematic front view of the embodiment of FIG. 4a;

FIG. 4c shows a skeletal schematic front view of the embodiment of FIG. 4a;

FIG. 6b shows a skeletal view of the embodiment of FIG. 6a;

FIG. 7b shows a top view the embodiment of FIG. 7a;

FIG. 8b shows a side view of the embodiment of FIG. 8a;

FIG. 8c shows another side view of the embodiment of FIG. 8a;

FIG. 8d shows a posterior view of the embodiment of FIG. 8a;

FIG. 9b shows a schematic anterior view of the embodiment of FIG. 9a;

FIG. 10b shows a schematic top view of the embodiment of FIG. 10a;

FIGS. 11a–c show three views of a ninth embodiment of an endoluminal prosthesis;

FIG. 12a shows a skeletal anterior view of a tenth embodiment of an endoluminal prosthesis;

FIG. 12b shows a schematic anterior view of the embodiment of FIG. 12a;

FIG. 12c shows a schematic top view of the embodiment of FIG. 12a;

FIG. 13b shows a skeletal view of the embodiment of FIG. 13a;

FIG. 13c shows a schematic top view of the embodiment of FIG. 13a;

FIGS. 14a–b show two views of a twelfth embodiment of an endoluminal prosthesis;

DETAILED DESCRIPTION

Figure 3A:
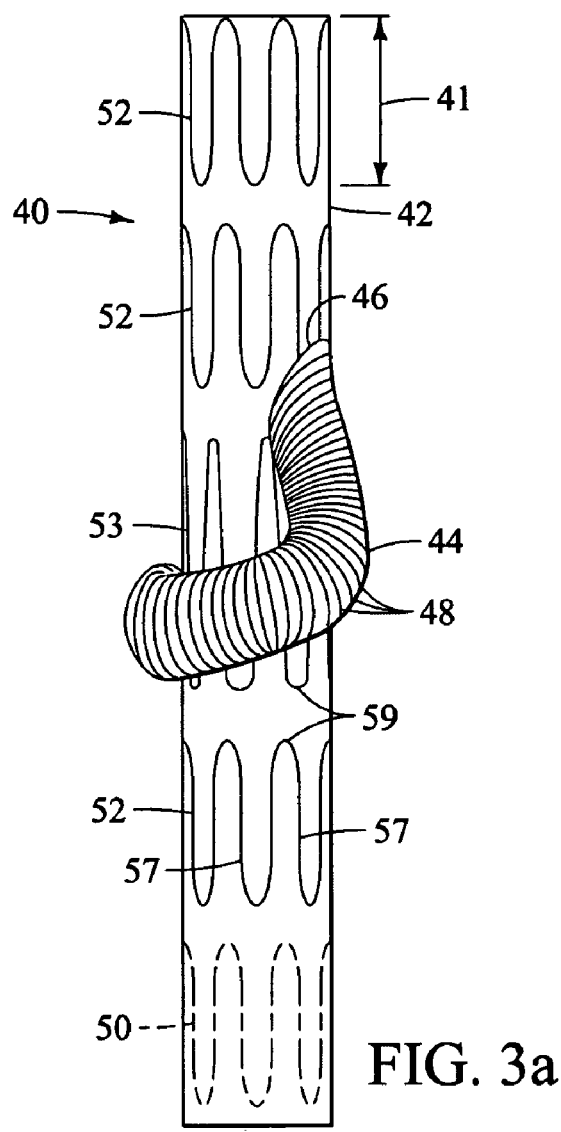
FIG. 3a shows a side view of a second embodiment of an endoluminal prosthesis with a helical prosthetic branch.

Branch vessel prostheses may be formed with prosthetic branches that are disposed longitudinally and circumferentially with respect to the prosthetic trunk. Such prosthetic branches are termed "helical" prosthetic branches. A branch extension may be connected to the distal end of the helical prosthetic branch by tromboning.

The helical turn in the prosthetic branch may reduce the forces on the branch extension by shifting the hemodynamic forces from the prosthetic branch and the interconnection between the branch extension to the prosthetic trunk. This may help prevent the branch extension from pulling out under those forces. The helical turn may also allow a wider variation in the radial orientation ("angle of access") of the prosthetic trunk and may prevent kinking of the prosthetic branch or branch extension. This design may also improve the hemodynamics by, for example, promoting laminar flow.

To help understand this description, the following definitions are provided.

The term "prosthesis" means any replacement for a body part or function of that body part. It can also mean a device that enhances or adds functionality to a physiological system.

The term "endoluminal" describes objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etc. An "endoluminal prosthesis" is thus a prosthesis that can be placed inside one of these lumens.

The term "stent" means any device or structure that adds rigidity, expansion force or support to a prosthesis. A Z-stent is a stent that has alternating struts and peaks (i.e., bends) and defines a generally cylindrical lumen. The "amplitude" of a Z-stent is the distance between two bends connected by a single strut. The "period" of a Z-stent is the total number of bends in the Z-stent divided by two, or the total number of struts divided by two.

The term "pull-out force" means the maximum force of resistance to partial or full dislocation provided by a modular prosthesis. The pull-out force of a prosthesis having two interconnected modules can be measured by an MTS ALLIANCE RT/5® tensile testing machine (MTS Corporation, Eden Prairie, Minn.). The MTS machine is connected to a computer terminal that is used to control the machine, collect, and process the data. A pressurization pump system is attached to the load cell located on the tensile arm of the MTS machine. One end of the prosthesis is connected to the pressurization pump, which provides an internal pressure of 60 mm Hg to simulate the radial pressure exerted by blood upon the device when deployed in vivo. The other end of the prosthesis is sealed. The prosthesis is completely immersed in a 37° C. water bath during the testing to simulate mean human body temperature. The MTS machine pulls the devices at 0.1 mm increments until the devices are completely separated. The computer will record, inter alia, the highest force with which the modules resist separation, i.e. the pull-out force.

The term "endoleak" refers to a leak around or through an endoluminal prosthesis. Endoleaks can occur through the fabric of a prosthesis, through the interconnections of a modular prosthesis, or around the ends of the prosthesis, inter alia. Endoleakage may result in the repressurizing of an aneurysm.

The term "branch vessel" refers to a vessel that branches off from a main vessel. Examples are the celiac and renal arteries which are branch vessels to the aorta, which is the main vessel in this context. As another example, the hypogastric artery is a branch vessel to the common iliac, which is a main vessel in this context. Thus, it should be seen that "branch vessel" and "main vessel" are relative terms.

The term "prosthetic trunk" refers to a portion of a prosthesis that shunts blood through a main vessel. A "trunk lumen" runs through the prosthetic trunk.

The term "prosthetic branch" refers to a portion of a prosthesis that is anastomosed to the prosthetic trunk and shunts blood into and/or through a branch vessel.

A "peripheral prosthetic branch" is a prosthetic branch that is anastomosed to the side of a prosthetic trunk. This is distinguished from a "contralateral prosthetic branch" which is a prosthetic branch that results from a "pant leg" bifurcation. The bifurcation may be asymmetrical, i.e. the two "legs" may have different diameters.

The term "branch extension" refers to a prosthetic module that can be deployed within a branch vessel and connected to a prosthetic branch.

The term "helical" or "helically" describes a prosthetic branch that is oriented circumferentially about and longitudinally along a prosthetic trunk. "Helical" is not restricted to a regular helix or a full 360° circumferential turn.

"Longitudinally" refers to a direction, position or length substantially parallel with a longitudinal axis of a reference, and is the length-wise component of the helical orientation.

"Circumferentially" refers to a direction, position or length that encircles a longitudinal axis of reference, and is the radial component of a helical orientation. Circumferential is not restricted to a full 360° circumferential turn nor a constant radius.

"Anastomosis" refers to a connection between two lumens, such as the prosthetic trunk and prosthetic branch that puts the two in fluid communication with each other. "Anastomosing" refers to the process of forming an anastomosis.

The term "angle of incidence" refers to the angle of intersection of a longitudinal axis of a prosthetic branch and a line on the prosthetic trunk that runs longitudinally through the anastomosis.

The term "skew" refers to the angle of out-of-plane rotation of the prosthetic branch, relative to the longitudinal axis of the prosthetic trunk, as measured at or near the anastomosis.

The term "angle of access" refers to the acceptable range of radial orientation of the branched prosthesis about the longitudinal axis of the prosthetic trunk. Through that range, the distal ostium of the prosthetic branch is close enough to the branch vessel so that the branch extension can be properly deployed into the branch vessel to form a connection with the prosthetic branch.

FIG. 1 shows a schematic representation of a prosthetic branch 12 anastomosed to the prosthetic trunk 10 in a y-configuration. A branch extension 14 forms a tromboning connection with the prosthetic branch 12. The branch extension 14 is positioned at a 45° angle 16 to the prosthetic trunk 10 to accommodate the anatomy in which the total prosthesis is designed to sit. The angle 16 of the branch extension 14 causes it to bear forces in the y-direction 15, as a result of the blood pressure and momentum of the blood flow through the prosthetic branch 12 and branch extension 14.

The connection between the branch extension 14 and the prosthetic branch 12 is maintained by friction forces. Therefore, if the forces in the y-direction 15 borne by the branch extension 14 exceed the friction forces that maintain the connection, the branch extension 14 may disconnect from the branch 12. This is a dangerous outcome for the patient, as the disconnection can result in a repressurization of the region surrounding the prosthetic branch 12 and the prosthetic trunk 10.

FIG. 2 shows a schematic representation of one embodiment of the present invention. In this embodiment, the prosthetic branch 22 is anastomosed to the prosthetic trunk 20. A branch extension 25 forms a tromboning connection with the prosthetic branch 22. The branch extension 25 is positioned at a about 60–70° angle 24 to the prosthetic trunk 20 to accommodate the anatomy in which the total prosthesis is designed to sit, although it can be placed at any suitable angle. The prosthetic branch 22 turns about the prosthetic trunk 20 to form a partial helix.

The angle 24 of the prosthetic branch 25 creates flow forces in the y-direction 23 as a result of the momentum of the blood flow through and physiological blood pressure in the branch 25, just as in the prosthesis of FIG. 1. However, unlike in FIG. 1, the prosthetic branch 22 bears much of these y-forces and is supported by its attachment 27 to the prosthetic trunk 20. Thus, the attachment 27 bears at least some of the y-direction forces instead of the load being placed on the interconnection 21. This helps prevent a common failure mode known in branched prostheses.

FIG. 3a shows another embodiment of the present invention. This embodiment is suitable for deployment into the left iliac artery and branching into the left hypogastric artery, although can be adapted for other vessels. An embodiment suitable for deployment into the right iliac artery could be a longitudinal mirror-image of the prosthesis 40 of FIG. 3a. The prosthesis 40 includes a prosthetic trunk 42 and a peripheral prosthetic branch 44. For this prosthesis 40 and the others discussed herein, the prosthetic branch 44 preferably curves around the anterior of the prosthetic trunk 42, as shown, although, as an alternative, may curve around the posterior of the prosthetic trunk 42. The prosthetic branch 44 is in fluid communication with the prosthetic trunk 42 through the anastomosis 46. The anastomosis 46 is preferably infundibular, i.e. funnel-shaped, as shown. This mimics a typical physiological anastomosis, and improves the hemodynamics of flow into the prosthetic branch 44. The prosthetic branch 44 is preferably sutured to the prosthetic trunk 42 to form a blood-tight seal. The proximal end of the prosthetic trunk may have a scallop cut into it in order to facilitate deployment of the prosthesis 40, described below.

The prosthetic trunk 42 is preferably made of woven polyester having a twill weave and a porostity of about 350 ml/min/cm$^2$ (available from VASCUTEK® Ltd., Renfrewshire, Scotland, UK). The prosthetic branch 44 is preferably made of seamless woven polyester. The prosthetic trunk 42 and prosthetic branch 44 can also be made of any other at least substantially biocompatible material including such fabrics as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS). Other examples of ECMs are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; U.S. Pat. No. 6,206,931 to Cook et al.; U.S. Pat. No. 6,358,284 to Fearnot et al.; 17 Nature Biotechnology 1083 (Nov. 1999); and WIPO Publication WO 98/22158 of May 28, 1998, to Cook et al., which is the published application of PCT/US97/14855. All of these references are incorporated herein by reference. It is also preferable that the material is non-porous so that it does not leak or sweat under physiologic forces.

The prosthetic branch 44 is preferably, but not necessarily connected to a branch extension. The prosthetic branch 44 and the branch extension 55 preferably have complementary annular crimps 48. Crimping decreases the risk of kinking, thereby helping preserve the patency of the prosthesis. Complementary crimping or other types of projections at the tromboning interconnection also help maintain the seal and prevent pull-out. Complementary projections on the overlapping modules tend to engage each other to maximize the surface contact between opposing contact surfaces.

The crimps shown in FIG. 3a may be created by mounting the prosthetic branch 44, for example, over a mandrel of substantially the same diameter. A thread, wire or other filament is wrapped helically around the prosthetic branch 44. The assembly as described is then heated to a temperature of 138° C. for eight (8) hours. Other temperatures can be used. Typically, the higher the temperature, the shorter the time required for adequate crimping, and vice versa. This induces helical crimping in the wrapped portion of the prosthesis. Annular crimps can also be generated by attaching annular filaments to the prosthetic branch 44 and performing the other steps of this process. The crimp peaks can be spaced by any suitable distance, preferably so that there are about 5 crimp peaks per 10 mm. The crimped interconnection and methods for producing crimps are described in greater detail in U.S. Provisional Patent Application entitled "Endoluminal Prosthesis With Interconnectable Modules," Ser. No. 60/510,617, filed Oct. 10, 2003, which is incorporated herein by reference.

The preferred size and shape of the prosthetic module 40 depends on the anatomy in which it is to be implanted and the corresponding module to which this prosthetic module 40 will be connected. Physiological variables, deployment characteristics and other factors also contribute to the determination of proper size and shape of the prosthetic trunk. The prosthetic trunk 42 preferably has a 12 mm diameter through its length, as shown, but may have a taper, turn or any other suitable geometry. The dimensions of any of the prostheses mentioned herein are only provided as an example, and will preferably be altered to match a particular patient's anatomy.

The stents 50, 52, 53 maintain the patency of the prosthesis and ensure adequate sealing against the surrounding vascular tissue. One goal for stent design and placement, whether internal or external, is to prevent metal-to-metal contact points, prevent contact between two different types of alloys and minimize micromotion. Stent sizing, spacing and design should be determined so that there is no stent-to-stent contact even in tortuous anatomy. Stents are preferably placed to maximize prosthesis flexibility while maintaining patency, as well as reduce material wear and stent fatigue. Furthermore, it is preferable that the stents do not interfere with the prosthetic branch, that they minimize the potential for galvanic corrosion and ensure adequate joint stability. Stent amplitude, spacing and stagger are preferably optimized for each prosthesis design. Any of the stents mentioned herein may have barbs to help decrease prosthesis migration.

The Z-stent design is preferred for straight sections of the aorta; it provides both significant radial force as well as some longitudinal support. In tortuous anatomy, branches or fenestrations, it may be preferable to use alternative stents or modifications to the Z-stent design to avoid stent-to-stent contact. Furthermore, in complex anatomic situations, external stents have the potential to become intertwined with the wires and other devices utilized to ensure branch vessel access, sealing and fixation. In some instance it may be desirable to affix some of the stents to the internal surface of the prosthesis. All of the stents mentioned herein are preferably made from standard medical grade stainless steel and are soldered using silver standard solder (0 lead/0 tin).

Stents 50, 52, 53 are affixed to the prosthesis 40 both internally 50 and externally 52, 53. Preferably Gianturco-type Z-stents of either 14 or 16 gauge (commercially available from Cook, Inc., Bloomington, Ind.) are employed, as shown. The stents 50, 52, 53 are preferably spaced 4 mm from each other, as measured peak-to-peak. The peaks 59 are preferably staggered for minimal contact with each other. The stents 50, 52 preferably have a 14 mm amplitude 41. The stent 53 nearest to the anastomosis 46 has a 22 mm amplitude, except near the anastomosis 46, where the amplitude is preferably 11 mm so that it does not interfere with the anastomosis 46. This stent 53 may be affixed internally.

At least one stent (not shown) is associated with the prosthetic branch 44; it is preferably attached just below the proximal seam 47 of the prosthetic branch 44. The stent is employed to keep the anastomosis 46 open and to prevent kinking upon bending of the prosthetic branch 44. PROLENE® 5-0 sutures (not shown) are preferably used for the distal sealing stent 50 while polyester 4-0 sutures (not shown) are used for all other stents 52, 53. Two conventional sutures are preferably tied to each strut 57, and one suture is preferably tied at each peak 59.

The angle of incidence of the prosthetic branch 44 is preferably about 20° to about 60°, and more preferably about 45° with respect to the prosthetic trunk 42; the skew is preferably about 0° to about 30° at the anastomosis 46. The prosthetic branch 44 is preferably anchored to prosthetic trunk 42 by three spaced sutures (not shown) no closer than about 4 mm from the anastomosis 46.

Standard endoluminal techniques may be used to deploy this prosthesis, as described below in further detail. An 18 French sheath may be used, unless loading issues warrant a larger sheath such as a 20 French. Standard radiopaque gold markers (Cook, Inc., Bloomington, Ind.) are preferably used to assist graft orientation when the prosthesis is viewed through a fluoroscope.

Figure 3C:
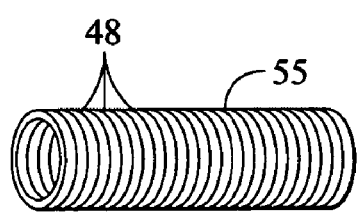
FIG. 3c shows an embodiment of an extension module.
Figure 3B:
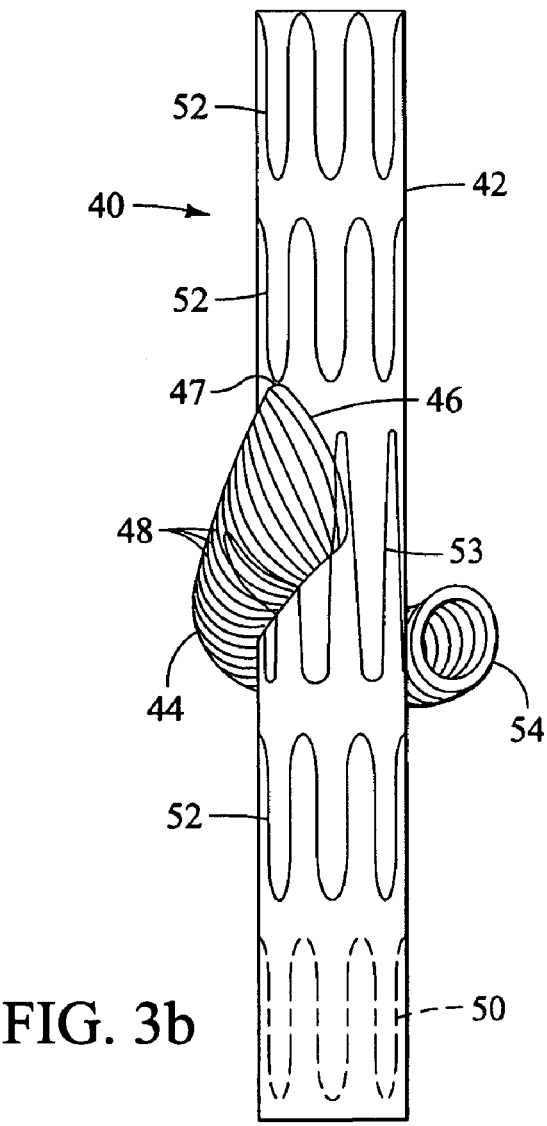

FIG. 3b is an alternative perspective of the prosthesis 40 of FIG. 3a. This shows the shape of the anastomosis 46. The size and shape of the anastomosis 46 may promote laminar flow and other positive hemodynamic characteristics. One method for creating this kind of anastomosis is described below in reference to FIG. 5.

After the prosthesis 40 is implanted, the distal ostium 54 of the prosthetic branch 44 is preferably positioned in the vicinity of the main vessel-branch vessel anastomosis. Then the branch extension 55, shown in FIG. 3c, can be implanted so that it forms a tromboning connection with the prosthetic branch 44. There is preferably a 1 mm or less difference in diameter at the interconnection between the distal ostium 54 of the prosthetic branch 44 and the branch extension 55 to encourage a sealing interconnection. The branch extension 55 may have stents, preferably internal stents, which are less likely to interfere with the seal or fit between corresponding crimps 48.

Figure 4A:
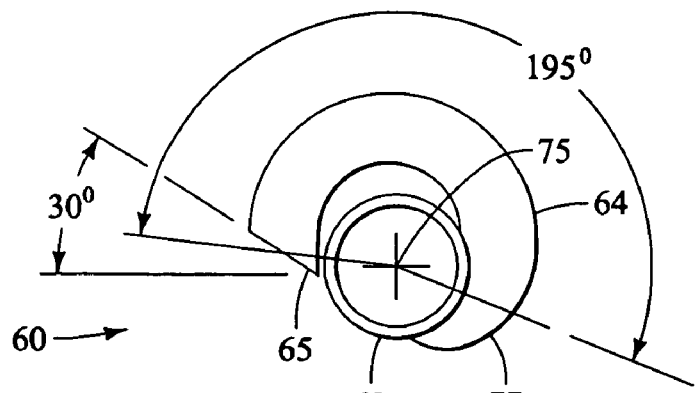
FIG. 4a shows a schematic top view of a third embodiment of an endoluminal prosthesis.
Figure 4B:
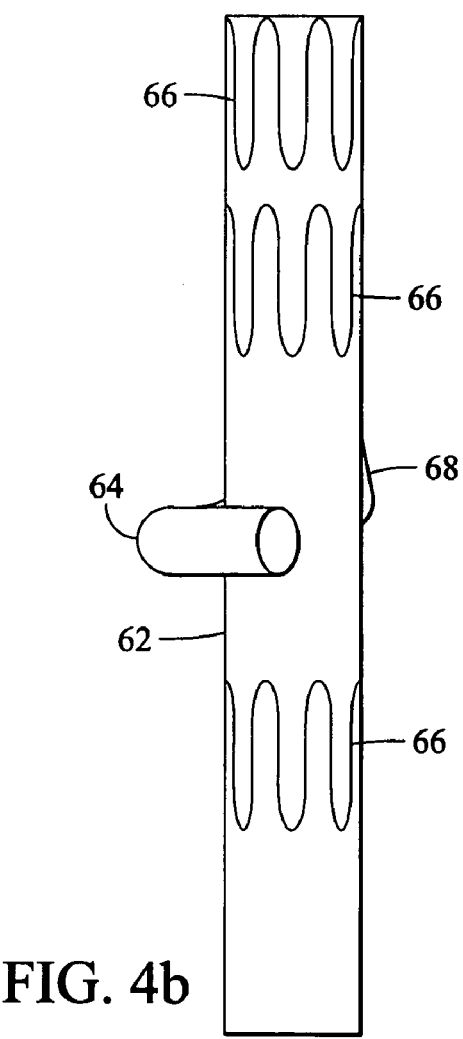
Figure 4C:
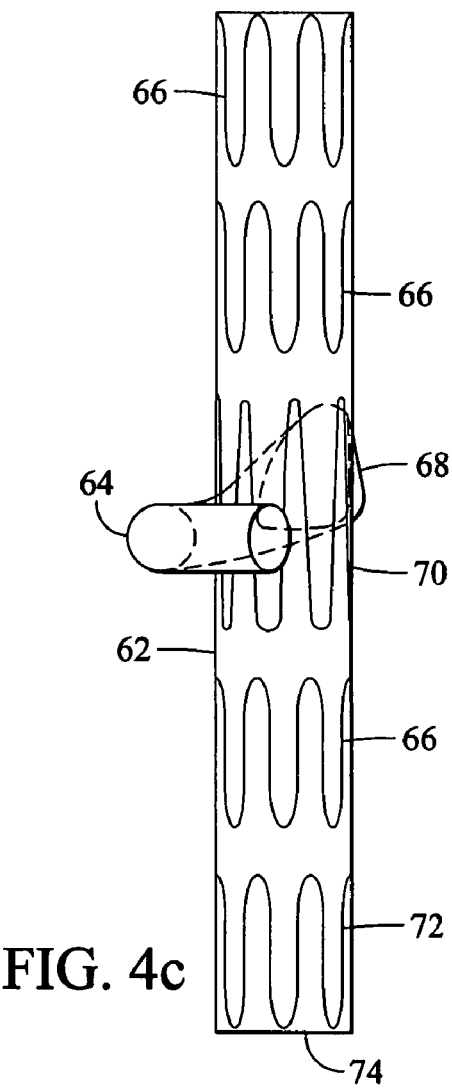

FIG. 4a shows a top view of a prosthesis 60 with a prosthetic trunk 62 and prosthetic branch 64. This prosthesis 60 is designed to be deployed into the right common iliac artery and branch to the right hypogastric artery, although can be adapted for deployment into other vessels. The prosthetic branch 64 is positioned longitudinally and circumferentially with respect to the prosthetic trunk 62, i.e. generally in the form of a helix about the longitudinal axis 75. The prosthetic branch 64 shown in FIG. 4a makes a 195° (or slightly more than one-half the circumference) turn about the prosthetic trunk 62 as measured from the midpoint 77 of the anastomosis to the midpoint of the distal ostium 65, as shown in FIG. 4a. This perspective shows that the distal ostium 65 of the prosthetic branch 64 is beveled by 30°. This may increase the access angle and ease of insertion for the branch extension. A side view of the prosthesis 60 of FIG. 4a is shown in FIGS. 4b and 4c. This prosthesis 60 has three external Z-stents 66 near the prosthetic trunk 62. FIG. 4c, a skeletal view of the prosthesis, shows an internal Z-stent 70 that straddles the anastomosis 68 and an internal stent 72 on the distal terminus 74. One method for forming the enlarged anastomosis 68 is shown in FIGS. 5a–d.

Figure 5A:
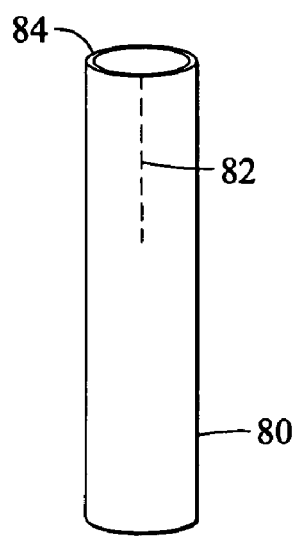
FIGS. 5a–d show preferable steps for creating an enlarged anastomosis.
Figure 5B:
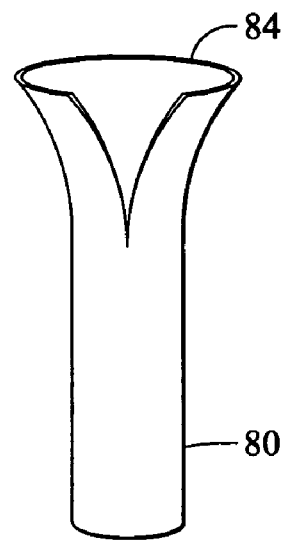
Figure 5C:
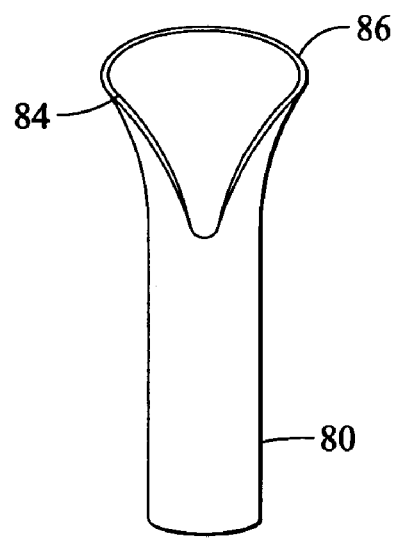
Figure 5D:
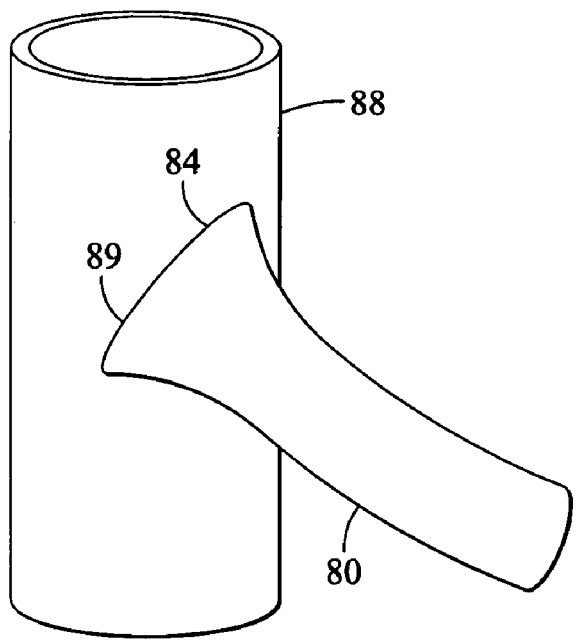

FIG. 5a shows a process for creating an enlarged or "tear-drop" anastomosis. The starting material for the prosthetic branch 80 is typically a tubular section of polyester prosthesis fabric. The proximal end 84 of the prosthetic branch 80 can be cut at a right angle to the longitudinal axis of the prosthetic branch 80, as shown, or can be beveled or otherwise shaped. The prosthetic branch 80 is cut along a line 82 at its proximal end 84. The line 82 does not have to be parallel to the axis of the tube. Then, as shown in FIG. 5b, the proximal end 84 is splayed. Following splaying, the proximal end 84 can be further shaped to form a new perimeter 86, as shown in FIG. 5c. The splayed perimeter 89 of the proximal end 84 shown in FIG. 5b is preferably sewn to the perimeter of a fenestration (not shown) in the prosthetic trunk 88 of a shape and size to match the splayed perimeter 89, as shown in FIG. 5d. The seam is preferably blood-tight. The fenestration can be oriented in any way relative to the axis of the prosthetic trunk 88 to skew the prosthetic branch 80. The prosthetic branch 80 is then preferably attached to the prosthetic trunk 88 such that it is positioned longitudinally and circumferentially in relation to the prosthetic trunk 88.

Figure 6A:
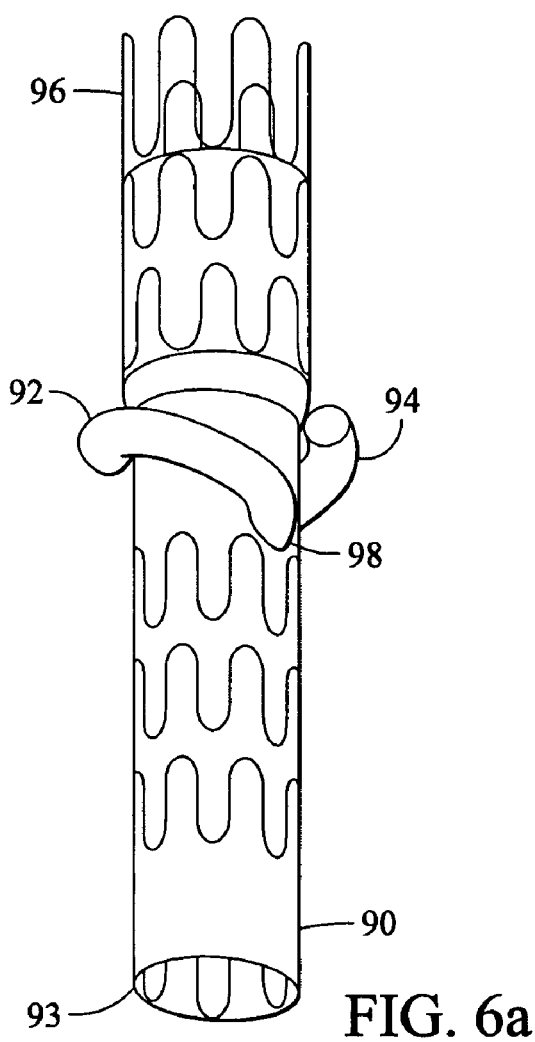
FIG. 6a shows a schematic anterior view of a fourth embodiment of an endoluminal prosthesis.
Figure 6B:
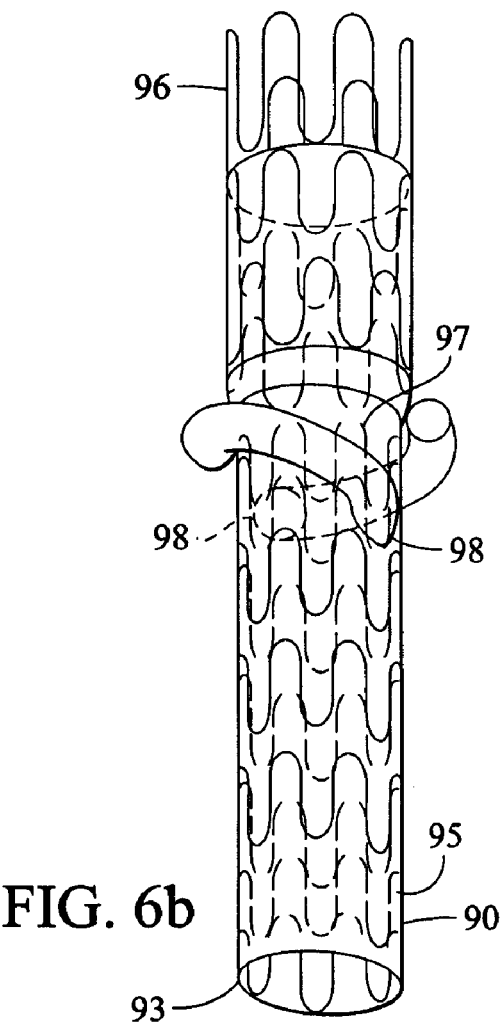

FIG. 6a shows a prosthesis 90 with two helical peripheral prosthetic branches 92, 94 extending therefrom. This prosthesis is designed to be positioned within the aorta so that the prosthetic branches 92, 94 can extend to the renal arteries, although this prosthesis design can be adapted for use in other vessels. Branch extensions can then be positioned within the renal arteries so that they form a tromboning connection with the prosthetic branches 92, 94. The uncovered stent 96 is a suprarenal fixation stent which may have barbs (not shown). A skeletal view of the prosthesis 90 of FIG. 6a is shown in FIG. 6b. The stent 95 closest to the distal end 93 of the prosthesis 90 is preferably attached internally, as is the stent 97 near the anastomosis. The anastomoses 98 can be as shown or can be the enlarged anastomosis described above with reference to FIG. 5. The prosthetic branches 92, 94 may slope away from the distal end 93 of the prosthesis 90, as shown, or towards the distal end 93 of the prosthesis 90. Stents (not shown) may be used to keep the prosthetic branches 92, 94 patent. Additional prosthetic branches may be anastomosed to the prosthesis 90 to shunt blood to the celiac, SMA, and/or other branch vessels.

Figure 7A:
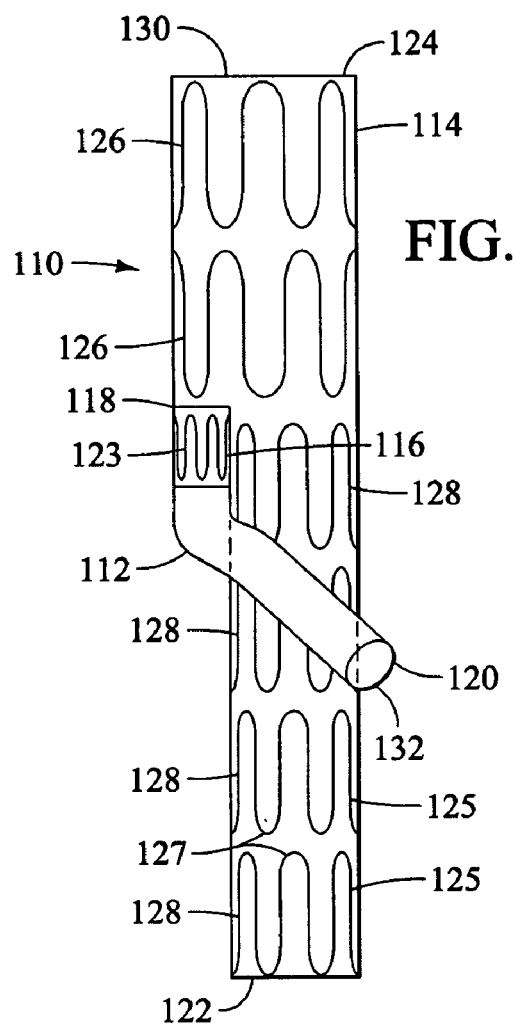
FIG. 7a shows a schematic anterior view of a fifth embodiment of an endoluminal prosthesis.

In FIG. 7a, a skeletal view of a prosthesis 110 with a helical contralateral prosthetic branch 112 is shown. The prosthesis 110 is designed for deployment into a right iliac artery and branching into the hypogastric. Distally to the bifurcation 116, the length of the prosthetic branch 112 is positioned longitudinally and circumferentially with respect to the prosthetic trunk 114 and is seamless along its length. The longitudinal and circumferential placement of the prosthetic branch 112 is secured with one or more sutures (not shown) near and more proximally from the distal ostium 120 of the prosthetic branch 112. For this and other prostheses, the prosthetic branch 112 may extend into the prosthetic trunk 114, proximally to the bifurcation 116, such that the branch lumen (not shown) originates within the lumen (not shown) of the prosthetic trunk 114.

The prosthesis 110 is preferably made from woven polyester described above; the prosthetic branch 112 is preferably crimped. The stents are attached using PROLENE® 5-0 sutures. Gold markers (not shown) are preferably attached to the prosthesis 110 in various locations to indicate the position and orientation of the prosthesis 110 under a fluoroscope.

An internal stent 123 is used in the prosthetic branch 112 slightly below the seam 118 and near the bifurcation 116 to keep the prosthetic branch 112 patent and prevent kinking; this stent 123 is preferably internal to the prosthesis 110, but can also be placed externally. The stent 123 is preferably 6 gauge in diameter, has an amplitude of 8 mm and a period of 6. Two prosthetic trunk stents 126 are attached proximally to the bifurcation 116; these stents 126 preferably have a 17 mm amplitude, a diameter of 20 gauge and a period of 9. The prosthesis 110 also has four stents 128 placed distally to the bifurcation 116; these stents 128 preferably have a 14 mm amplitude, a diameter of 14 gauge and a period of 7. The stents 126, 128 are spaced about 4 mm from each other and the peaks 127 of the distal stents 128 are staggered to minimize contact between them. The two most distal stents 125 on the prosthetic trunk 114 can be affixed internally to prevent interference with the deployment of the branch extension.

The distal ostium 120 of the prosthetic branch 112 is preferably 6 mm in diameter. The distal end 122 of the prosthetic trunk 114 is preferably 14 mm in diameter; the proximal ostium 130 of the prosthetic trunk 114 is preferably 20 mm in diameter. The diameter of the prosthetic trunk 114 may be reduced to 12 mm. The distance between the proximal end 124 of the prosthetic trunk 114 to the distal end 132 of the prosthetic branch 112 is preferably about 65 mm. These dimensions are only provided as an example and may be varied to match the anatomy of a specific patient.

Figure 7B:
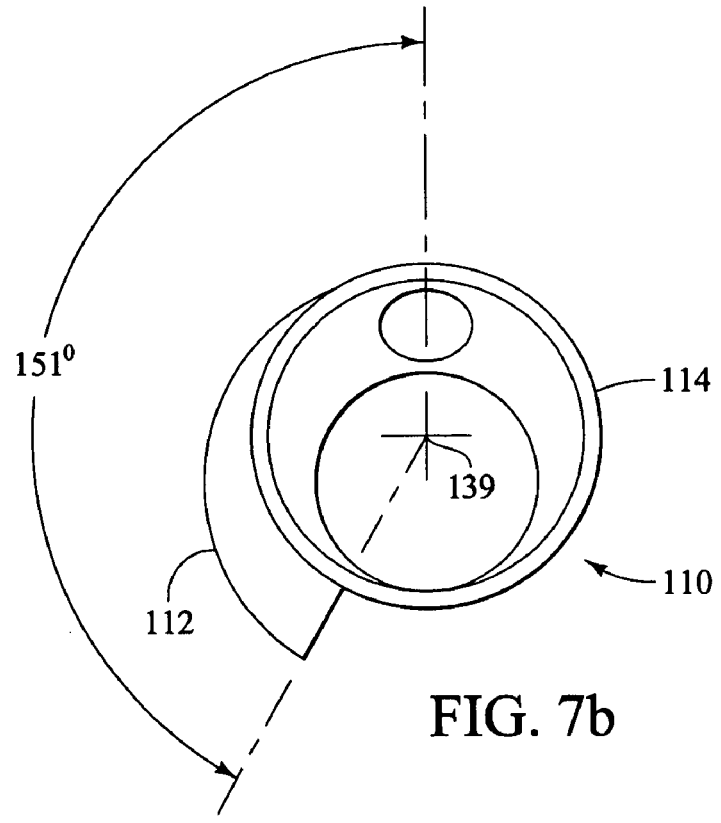

FIG. 7b shows a schematic top view of the prosthesis of FIG. 7a. The prosthetic branch 112 preferably turns 151° about the longitudinal axis 139 of the prosthetic trunk 114.

Figure 8A:
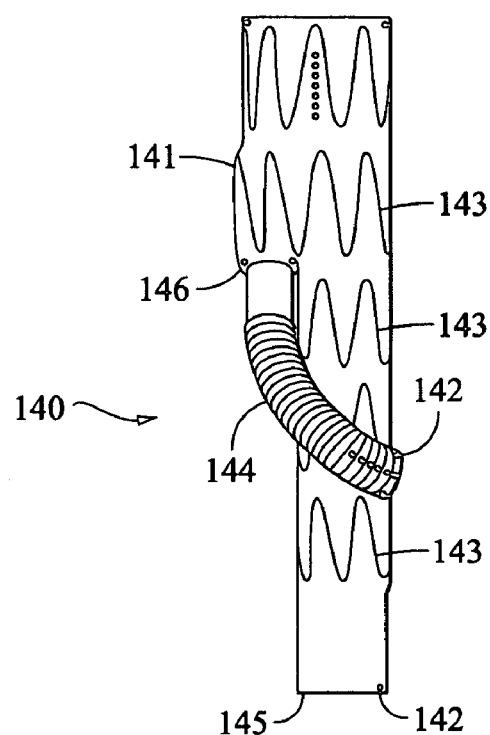
FIG. 8a shows an anterior view of a sixth embodiment of an endoluminal prosthesis.
Figure 8B:
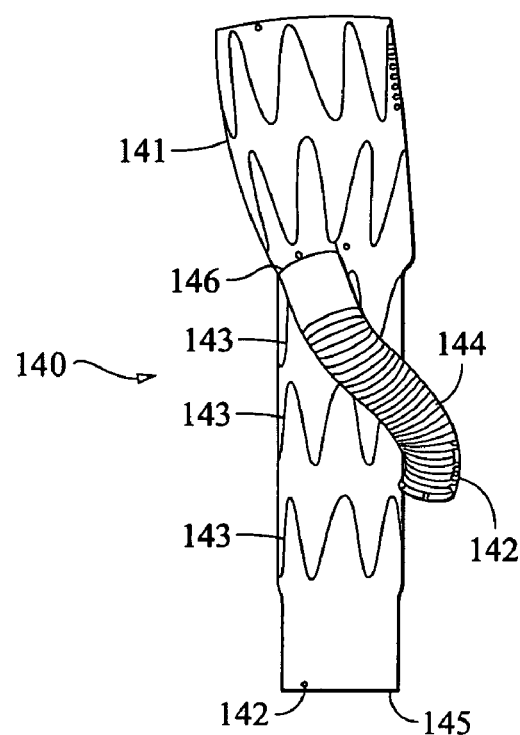
Figure 8C:
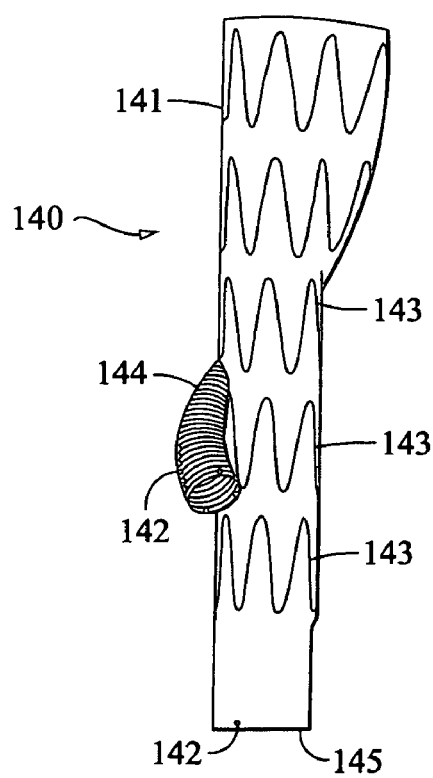
Figure 8D:
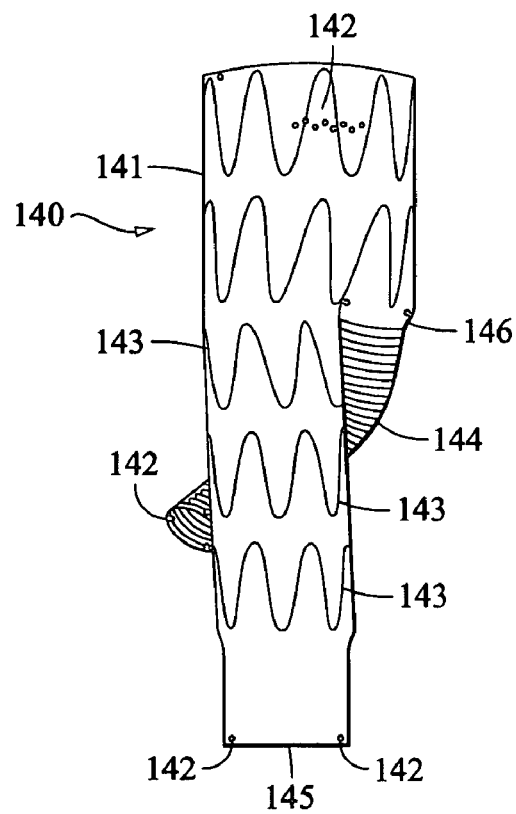

FIGS. 8a–d show different perspectives of a contralateral branched prosthesis 140 similar to the branched prosthesis described in FIGS. 7a–b. This prosthesis 140 is designed for deployment into a right iliac artery and branching into the right hypogastric. Radiopaque markers 142 are sewn to the prosthesis 140. The prosthetic branch 144 is preferably made of woven, crimped polyester. In FIG. 8d, the seam 146 between the prosthetic branch 144 and the prosthetic trunk 141 is evident. The stent (not shown) nearest to the distal end 145 of the prosthetic trunk 141 is attached internally. Any or all of the external stents 143 positioned distally to the seam 146 may be moved internally. Also, the prosthetic branch 144 at the seam 146 could be beveled; this would provide a larger ostium.

Figure 9A:
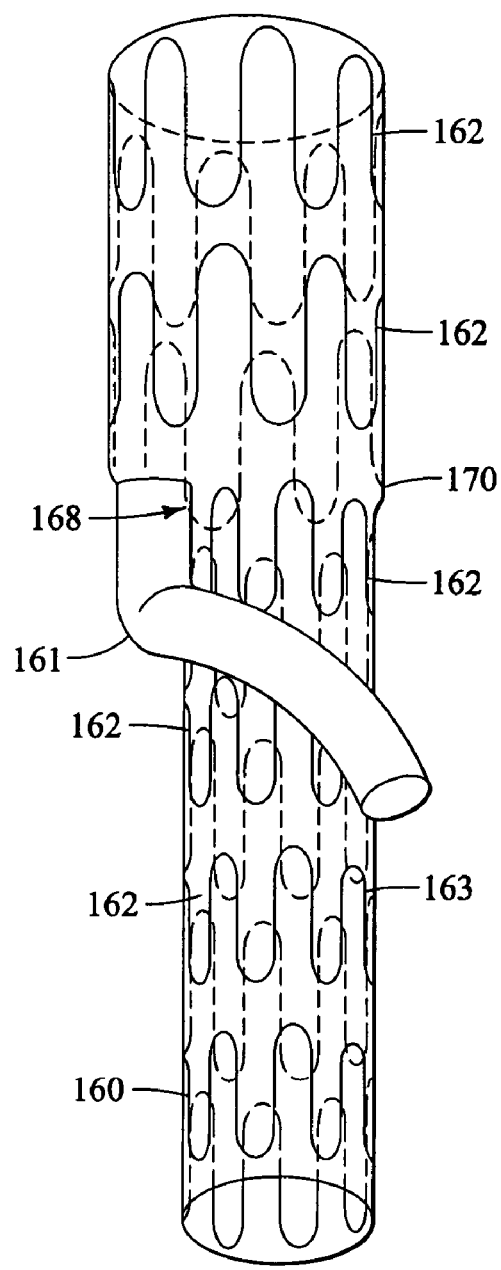
FIG. 9a shows a skeletal anterior view of a seventh embodiment of an endoluminal prosthesis.
Figure 9B:
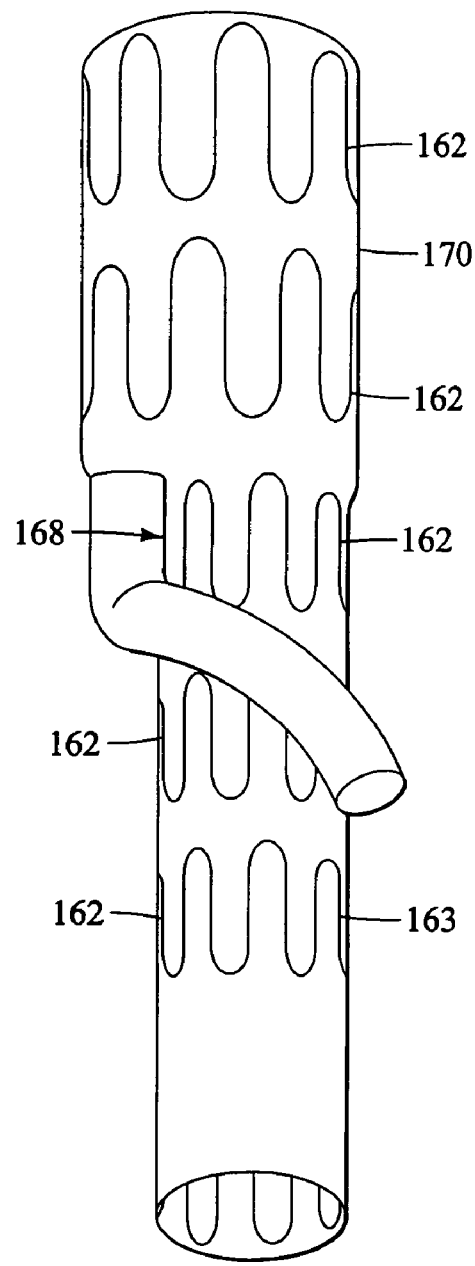

FIGS. 9a–b show an additional embodiment of the contralateral branched prosthesis similar to that described in reference to FIG. 7. FIG. 9a is a skeletal view, showing both the internal stent 160 and the external stents 162. The prosthesis of FIG. 9 has a prosthetic branch 161 that extends vertically down from the bifurcation 168 and then bends around the prosthetic trunk 170. The second most distal stent 163 can also be affixed internally.

Figure 10A:
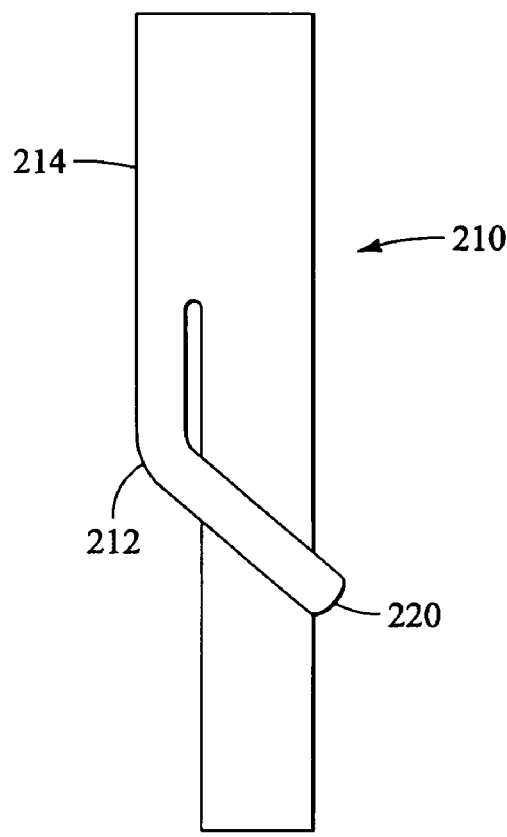
FIG. 10a shows a schematic anterior view of an eighth embodiment of an endoluminal prosthesis.
Figure 10B:
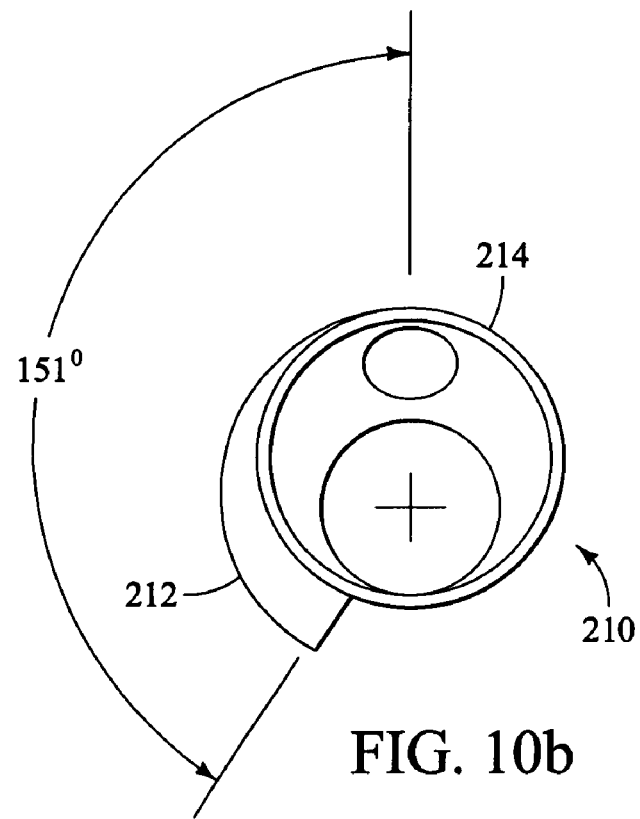

FIGS. 10a–b are schematic representations of the prosthesis described in reference to FIGS. 11a–c, below, and show another embodiment of a contralateral branched prosthesis 210. This prosthesis 210 is designed for deployment into the common iliac and branching into the hypogastric, although it can be adapted for use in any branched vessel. The longitudinal and circumferential placement of the prosthetic branch 212 is secured with one or more sutures near the distal end 220 of the prosthetic branch 212 and more proximally from the distal end 220. The prosthesis 210 is preferably made from woven polyester; the prosthetic branch 212 is crimped polyester. FIG. 10b shows the relative orientation of the prosthetic branch 212 to the prosthetic trunk 214; the prosthetic branch 212 preferably turns 151° helically around the prosthetic trunk 214.

FIGS. 11a–c show a branched contralateral prosthesis 211 suitable for deployment within the right iliac artery and branching into the hypogastric artery. The prosthetic trunk 233 has a proximal section 217 with a diameter of about 20 mm and a distal section 219 with a diameter of about 12 mm. The prosthetic branch 213 originates at the 20 mm diameter proximal section 217 and has a helical path about the 12 mm distal section 219. The helical path of the prosthetic branch 213 is approximately 180° in circumference and approximately 60 mm longitudinally from the seam 225. The pitch is preferably about 45°. The prosthetic branch 213 is preferably 6 mm in diameter through its length and constructed of crimped polyester graft material.

An internal stent 223, shown in FIG. 11a, slightly overlaps the seam 225 so that it is flush with the bifurcation 227 to keep the ostium open and prevent kinking upon bending of the prosthetic branch 213. This stent 223 is preferably attached to the internal surface of the prosthesis 211, but can also be placed externally. The stent 223 is preferably 6 gauge in thickness, 8 mm in height and preferably has a period of 6. Two stents 226 are attached proximally to the bifurcation 227; these stents 226 preferably have an 18 mm amplitude, a diameter of 20 gauge and a period of 10, and are spaced from each other by 2 mm. The prosthesis 211 also has four stents 228 placed distally to the bifurcation 227; these stents 228 have a preferred 14 gauge thickness, 14 mm amplitude, a period of 7, and are spaced by 3 mm. The two most distal stents 229 are preferably attached internally. The stents are preferably attached using PROLENE® 5-0. Gold markers 215 are attached to the prosthesis 211 in various locations to indicate the position of the prosthesis 211 under a fluoroscope.

The distal ostium 220 of the prosthetic branch 213 is preferably 6 mm in diameter; the distal end 222 of the prosthetic trunk 214 is preferably 12 mm in diameter; the proximal ostium 230 of the prosthetic trunk 214 is preferably 20 mm in diameter. The dimensions of this prosthesis 211, like the other prostheses described herein, are preferably matched to the anatomy of a specific patient. The peaks 231 of the prosthetic trunk stents 226, 228 are staggered to minimize contact between them. The distance between the proximal end 224 of the prosthetic trunk 214 to the distal ostium 222 of the prosthetic branch 212 is preferably about 70 mm. Deployment of this prosthesis 211 is made easier by the helical design, which allows the "angle of access" to be about 3 times greater than in y- or t-shaped branched prostheses.

FIG. 12a shows a skeletal view of a peripheral branched prosthesis 250. The prosthetic branch 252 of this prosthesis 250 extends at an angle from the side of the prosthetic trunk 254 and then bends back to the prosthetic trunk 254 where it is affixed with sutures. There is a gap 256 between the prosthetic branch 252 and the prosthetic trunk 254. The prosthetic branch 252 is preferably crimped (not shown), seamless and about 6 mm in diameter through its length. The prosthetic trunk 254 is seamless and about 12 mm in diameter through its length. The prosthetic branch 252 is anastomosed to the prosthetic trunk 254 between first 253 and second 255 proximal stents.

FIG. 12b is an external view of the prosthesis of FIG. 12a. As shown, only the top two stents 253, 255 are attached externally to the prosthesis 250. The other stents shown in FIG. 12a are attached internally. The stents 253, 255 that are around the anastomosis 259 may be affixed internally so that they do not catch on guide wires (not shown) used in deployment of the prosthesis 250. FIG. 12c shows a top view of the prosthesis of FIGS. 12a and 12b. The prosthetic branch 252 turns 137° around the prosthetic trunk 254, and is attached to the prosthetic trunk 254 at a location 261.

Figure 13A:
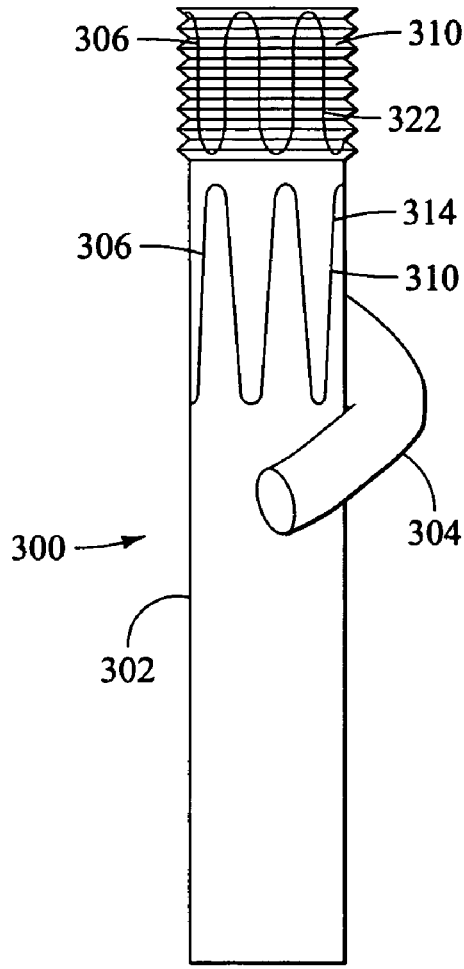
FIG. 13a shows a schematic anterior view of an eleventh embodiment of an endoluminal prosthesis.

An external view of a peripheral branched prosthesis 300 is shown in FIG. 13a. The prosthetic trunk 302 and the prosthetic branch 304 are both preferably made from polyester. The prosthetic branch 304 is preferably crimped (not shown) and seamless. Z-stents 306 of both 14 mm and 22 mm amplitudes are preferably attached to the prosthesis 300 with sutures (not shown). PROLENE® 5-0 is used to attach the distal stents 312; polyester 4-0 is used to attach the proximal stents 310. Gold markers (not shown) may be employed.

Figure 13B:
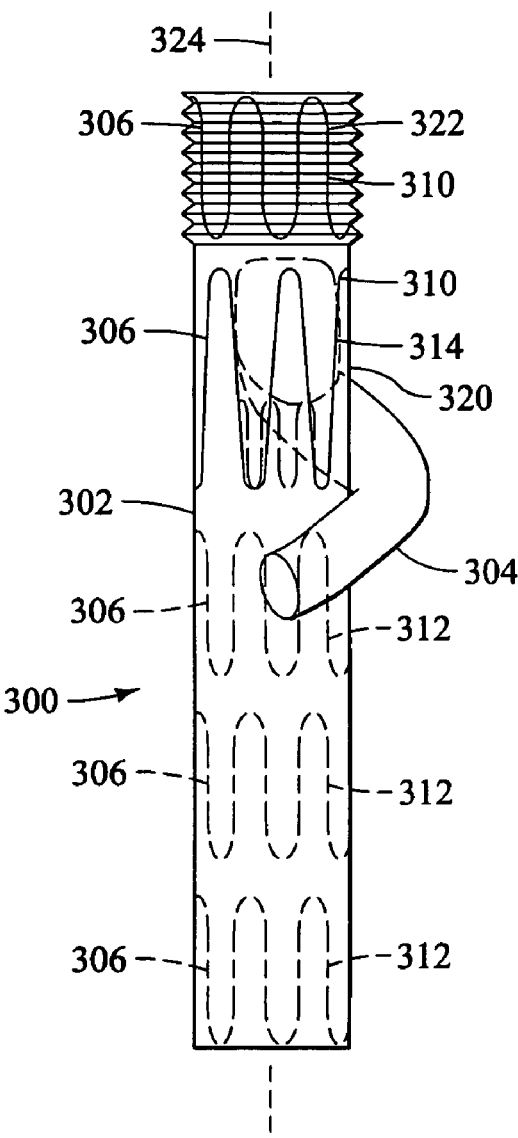

The prosthetic trunk 302 is preferably straight, having a consistent 12 mm diameter throughout. The stent 314 that abuts the prosthetic branch 302 has an amplitude of 22 mm, except as shown in FIG. 13b where the amplitude is 11 mm near the anastomosis 320. This stent 314 is preferably attached externally, as shown; it may be affixed internally. The angle of incidence of the prosthetic branch 304 to the prosthetic trunk 302 at the anastomosis 320 can range from about 20° to about 60°, and is preferably about 45°; the skew relative to the longitudinal axis 324 is preferably between about 0° to about 20° and more preferably about 0°. The length of the prosthetic branch 304 is adjacent to the prosthetic trunk 302; this may improve the distribution of material to reduce packing density during deployment of the prosthesis 300. The prosthetic branch 304 is anchored to prosthetic trunk 302 about 4 mm from the anastomosis 320 using about three sutures; they may be affixed further away to ensure the flexibility of the anastomosis 320.

The most proximal stent 322 is preferably of a 14 mm amplitude and attached externally to the prosthesis 300. The material underneath the most proximal stent 322 is crimped for superior mating to a proximal prosthesis; this stent 322 may also be attached to the inside surface of the prosthesis 300. The enlarged anastomosis 320 described above in reference to FIG. 5 is used to connect the prosthetic branch 304 to the prosthetic trunk 302. The three distal stents 312 are attached internally.

Figure 13C:
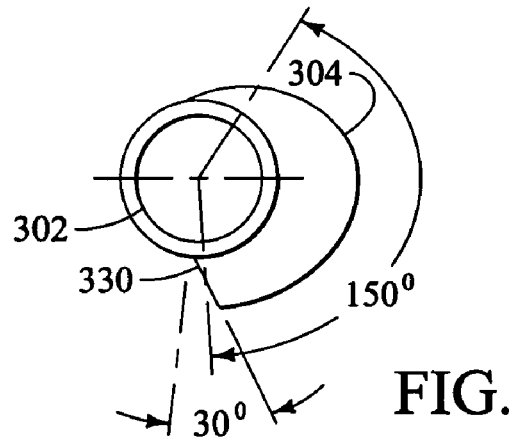

FIG. 13c shows a top view of the prosthesis of FIGS. 13a–b. The prosthetic branch 304 preferably wraps about 150° around the prosthetic trunk 302. The distal ostium 330 of the prosthetic branch 304 is preferably beveled about 30°.

FIGS. 14a–b show a prosthesis 350 that is similar to that described in reference to FIG. 13. The prosthetic branch 352 is preferably made from crimped polyester fabric. The region under the proximal stent 358 is crimped. The anastomosis 354 is the enlarged kind described above in reference to FIG. 5. The prosthetic branch 352 is skewed relative to the longitudinal axis 356 of the prosthesis 350 and has an angle of incidence preferably of about 30° to about 40°. The bevel of the prosthetic branch 304 is may be trimmed to provide greater clearance for the top stent 358.

Figure 15:
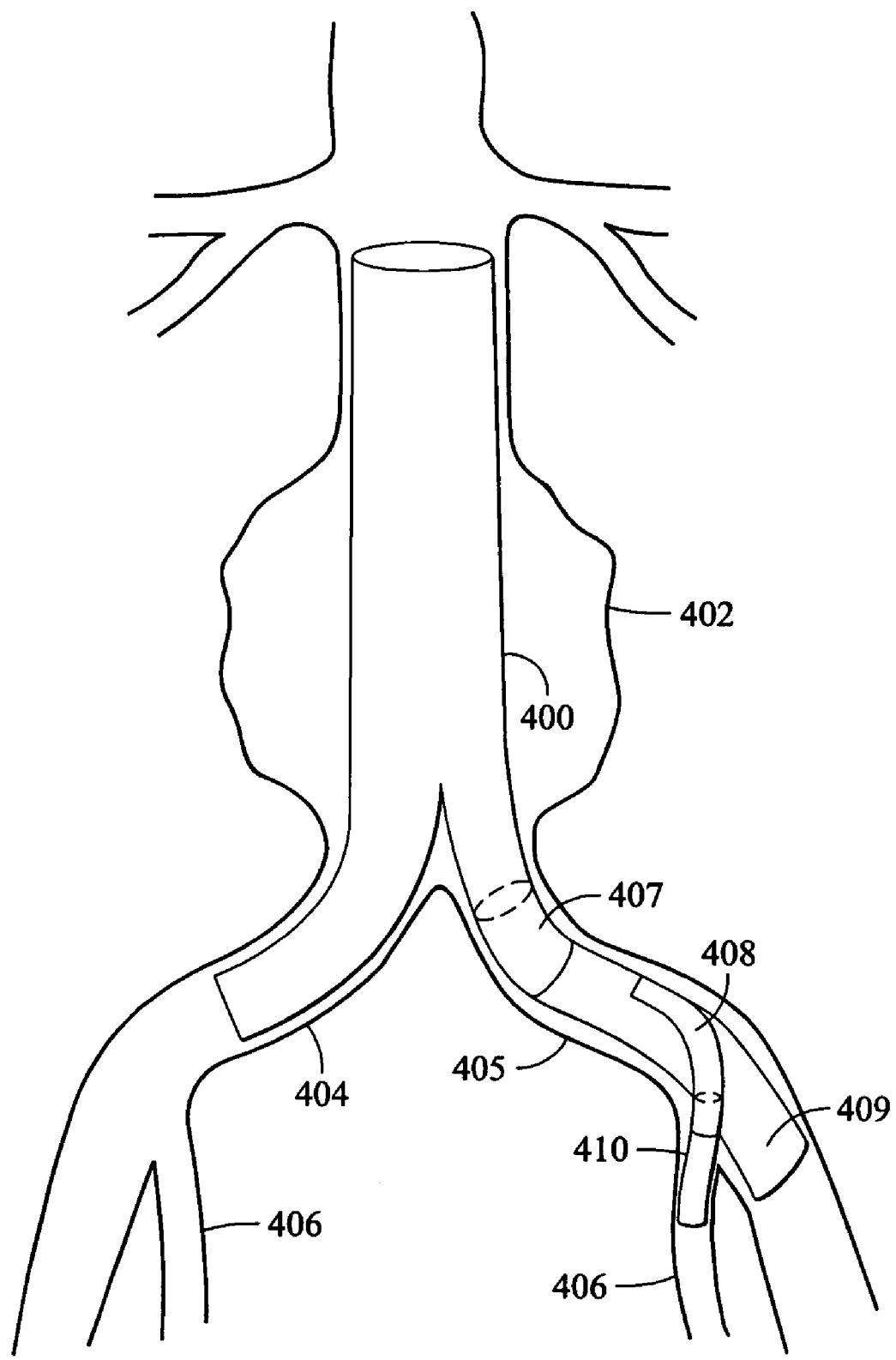
FIG. 15 shows a modular prosthesis that has a prosthetic trunk in the left iliac artery connected to a prosthetic branch in the hypogastric artery.

FIG. 15 shows a schematic representation of a bifurcated endoluminal prosthesis 400 implanted into an aneurysmal aorta 402. The prosthesis 400 extends into the iliac arteries 404, 405. One of the iliac limbs 407 forms a tromboning interconnection with an iliac extension 409, which, in this context is the prosthetic trunk. The iliac extension (i.e. prosthetic trunk) 409 is anastomosed to a helical prosthetic branch 408. The helical prosthetic branch 408 forms a tromboning interconnection with the hypogastric branch extension 410 which sites in the hypogastric artery 406.

Since arterial anatomy and aneurysm topology vary between patients, any of the prosthesis designs described above is preferably modified to accommodate a particular patient's need. The first step is to review the patient's CT scans. The critical parameters for prosthesis design (deployment site, proximal and distal sealing points) for the device needed for each patient are defined. A three-dimensional (3-D) model of the aneurysm is created using techniques known to one of skill in the art.

The aneurysm model can be incorporated into Solid Works™ or other suitable solid and surface modeling software. With this software a 3-D endoluminal prosthesis can be designed based on the aneurysm model and the defined critical parameters. A mechanical drawing is developed from the 3-D device. The mechanical drawing specifications are then used to create the component materials for the prototype prosthesis, including the prosthesis fabric and stents. Then the material and stents are assembled to form the final prosthesis.

A Modular Prosthesis and Introducer

Modular prostheses are known for use in treating descending thoracic and abdominal aortic aneurysms, where the prosthesis at the proximal end defines a single lumen for placement within the aorta and at the other end is bifurcated for extension into the iliac arteries. Iliac extension prosthetic modules can be connected to the ends of the bifurcation. A schematic view of such a prosthesis is described in further detail in PCT application WO98/53761.

WO98/53761 discloses a prosthesis which includes a sleeve or tube of biocompatible prosthesis material such as polyester fabric or polytetrafluoroethylene (PTFE) defining a single-lumen portion and a bifurcation, and further includes several stents secured therealong. The prosthesis is designed to span an aneurysm that extends along the aorta proximally from the two iliac arteries. This reference also discloses the manner of deploying the stent prosthesis in the patient utilizing an introducer assembly.

In the WO98/53761 application, the material-covered portion of the single-lumen proximal end of the prosthesis bears against the wall of the aorta above the aneurysm to seal the aneurysm at a location that is spaced distally of the entrances to the renal arteries. Thin wire struts of a proximal attachment stent traverse the renal artery entrances without occluding them, while anchoring the prosthesis in position within the aorta.

An extension module is affixed to one of the legs of the prosthesis to extend along a respective iliac artery and, optionally, extensions may be affixed to both legs. These extension modules are attached by tromboning. The deployment of a modular endoluminal prosthesis into the lumen of a patient from a remote location by the use of a deployment device or introducer is disclosed in the same patent application. PCT application WO98/53761 is incorporated herein by reference.

One modular prosthesis similar to that described in WO98/53761, the ZENITH® AAA Endovascular Graft sold by Cook, Inc., has been approved by the Food and Drug Administration (FDA) to treat aortic aneurysms. The ZENITH® AAA Endovascular Graft is made up of three prosthetic modules: a main body module and two leg modules. The main body is positioned in the aorta. The legs are positioned in the iliac arteries and connect to the main body. The prosthesis thus extends from the aorta below the renal arteries into both iliac arteries. The prosthesis itself is made of a polyester material like that used in open surgical repair. Standard surgical suturing techniques are used to sew the graft material to a frame of stainless steel stents. These self-expanding stents provide support for the graft material.

Figure 16:
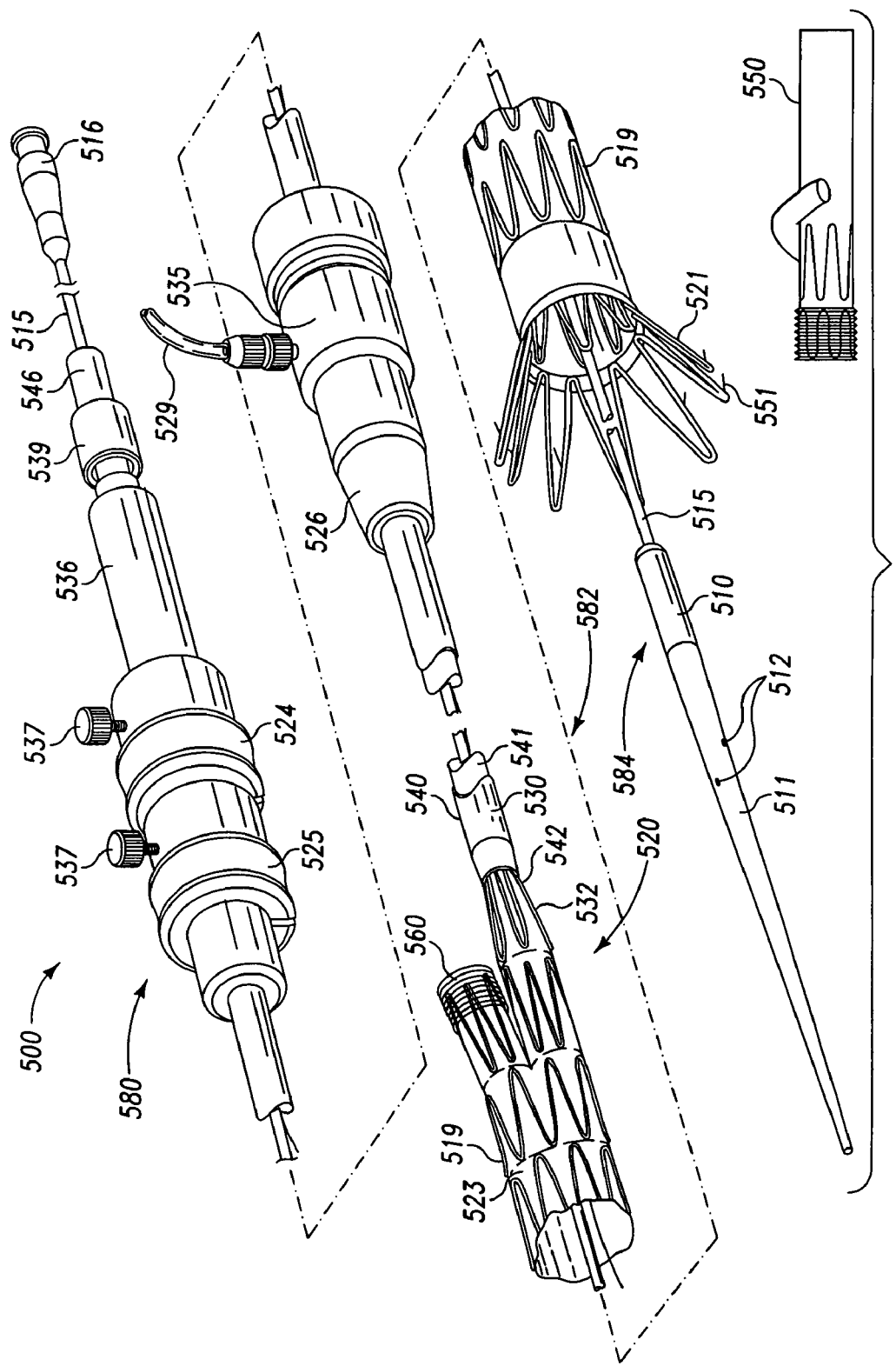
FIG. 16 shows an apparatus for deploying a bifurcated prosthesis.

FIG. 16 shows a ZENITH® self-expanding bifurcated prosthesis 520 (product code TFB1 through TFB5, available from Cook, Inc., Bloomington, Ind.), and an endovascular deployment system 500, also known as an introducer 500, for deploying the prosthesis 520 in a lumen of a patient during a medical procedure. These items are each described in greater detail in PCT application WO98/53761. A self-expanding branched prosthesis 550 similar to that described in reference to FIG. 13b is also shown.

The bifurcated prosthesis 520 has a generally inverted Y-shaped configuration. The prosthesis 520 includes a body 523, a shorter leg 560 and a longer leg 532. The bifurcated prosthesis 520 comprises a tubular graft material, such as polyester, with self-expanding stents 519 attached thereto. The self-expanding stents 519 cause the prosthesis 520 to expand following its release from the introducer 500. The prosthesis 520 also includes a self-expanding Z-stent 521 that extends from its proximal end. The self-expanding Z-stent 521 has distally extending barbs 551. When it is released from the introducer 500, the self-expanding Z-stent 521 anchors the barbs 551, and thus the proximal end of the prosthesis 520, to the lumen of the patient. As an alternative to the prosthesis 520 shown in FIG. 16, a prosthesis such as that shown in FIG. 6 could be deployed followed by renal branch extensions; this would have the added benefit of excluding any aneurysmal tissue in the renal arteries and allowing the aortic graft to extend further proximally. The self-expanding branched prosthesis 550 is similar to the branched prosthesis described in reference to FIG. 13b and is configured to form a tromboning connection with the shorter leg 560 of the bifurcated prosthesis 520 and with a branch extension. A notch or scallop may be cut into the proximal end of the branched prosthesis 550 to facilitate deployment of the module.

The introducer 500 includes an external manipulation section 580, a distal attachment region 582 and a proximal attachment region 584. The distal attachment region 582 and the proximal attachment region 584 secure the distal and proximal ends of the prosthesis 520, respectively. During the medical procedure to deploy the prosthesis 520, the distal and proximal attachment regions 582 and 584 will travel through the lumen to a desired deployment site. The external manipulation section 580, which is acted upon by a user to manipulate the introducer, remains outside of the patient throughout the procedure.

The proximal attachment region 584 of the introducer 500 includes a cylindrical sleeve 510. The cylindrical sleeve 510 has a long tapered flexible extension 511 extending from its proximal end. The flexible extension 511 has an internal longitudinal aperture (not shown). This longitudinal aperture facilitates advancement of the tapered flexible extension 511 along an insertion wire (not shown). The longitudinal aperture also provides a channel for the introduction of medical reagents. For example, it may be desirable to supply a contrast agent to allow angiography to be performed during placement and deployment phases of the medical procedure.

A thin walled metal tube 515 is fastened to the extension 511. The thin walled metal tube 515 is flexible so that the introducer 500 can be advanced along a relatively tortuous vessel, such as a femoral artery, and so that the distal attachment region 582 can be longitudinally and rotationally manipulated. The thin walled metal tube 515 extends through the introducer 500 to the manipulation section 580, terminating at a connection means 516.

The connection means 516 is adapted to accept a syringe to facilitate the introduction of reagents into the thin walled metal tube 515. The thin walled metal tube 515 is in fluid communication with the apertures 512 of the flexible extension 511. Therefore, reagents introduced into connection means 516 will flow to and emanate from the apertures 512.

A plastic tube 541 is coaxial with and radially outside of the thin walled metal tube 515. The plastic tube 541 is "thick walled"—its wall is preferably several times thicker than that of the thin walled metal tube 515. A sheath 530 is coaxial with and radially outside of the plastic tube 541. The thick walled plastic tube 541 and the sheath 530 extend distally to the manipulation region 580.

During the placement phase of the medical procedure, the prosthesis 520 is retained in a compressed condition by the sheath 530. The sheath 530 extends distally to a gripping and hemostatic sealing means 535 of the external manipulation section 580. During assembly of the introducer 500, the sheath 530 is advanced over the cylindrical sleeve 510 of the proximal attachment region 584 while the prosthesis 520 is held in a compressed state by an external force. A distal attachment (retention) section 540 is coupled to the thick walled plastic tube 541. The distal attachment section 540 retains a distal end 542 of the prosthesis 520 during the procedure. Likewise, the cylindrical sleeve 510 retains the self-expanding Z-stent 521.

The distal end 542 of the prosthesis 520 is retained by the distal attachment section 540. The distal end 542 of the prosthesis 520 has a loop (not shown) through which a distal trigger wire (not shown) extends. The distal trigger wire extends through an aperture (not shown) in the distal attachment section 540 into an annular region between the thin walled tube 515 and the thick walled tube 541. The distal trigger wire extends through the annular space to the manipulation region 580. The distal trigger wire exits the annular space at a distal wire release mechanism 525.

The external manipulation section 580 includes a hemostatic sealing means 535. The hemostatic sealing means 535 includes a hemostatic seal (not shown) and a side tube 529. The hemostatic sealing means 535 also includes a clamping collar (not shown) that clamps the sheath 530 to the hemostatic seal, and a silicone seal ring (not shown) that forms a hemostatic seal around the thick walled plastic tube 541. The side tube 529 facilitates the introduction of medical reagents between the thick walled tube 541 and the sheath 530.

A proximal portion of the external manipulation section 580 includes a release wire actuation section that has a body 536. The body 536 is mounted onto the thick walled plastic tube 541. The thin walled tube 515 passes through the body 536. The distal wire release mechanism 525 and the proximal wire release mechanism 524 are mounted for slidable movement onto the body 536.

The positioning of the proximal and distal wire release mechanisms 524 and 525 is such that the proximal wire release mechanism 524 must be moved before the distal wire release mechanism 525 can be moved. Therefore, the distal end 542 of the prosthesis 520 cannot be released until the self-expanding Z-stent 521 has been released, and the barbs 551 have been anchored to the lumen. Clamping screws 537 prevent inadvertent early release of the prosthesis 520. A hemostatic seal (not shown) is included so that the release wires can extend out through the body 536 without unnecessary blood loss during the medical procedure.

A distal portion of the external manipulation section 580 includes a pin vise 539. The pin vise 539 is mounted onto the distal end of the body 536. The pin vise 539 has a screw cap 546. When screwed in, vise jaws (not shown) of the pin vise 539 clamp against or engage the thin walled metal tube 515. When the vise jaws are engaged, the thin walled tube 515 can only move with the body 536, and hence the thin walled tube 515 can only move with the thick walled tube 541. With the screw cap 546 tightened, the entire assembly can be moved together as one piece.

Figure 17:
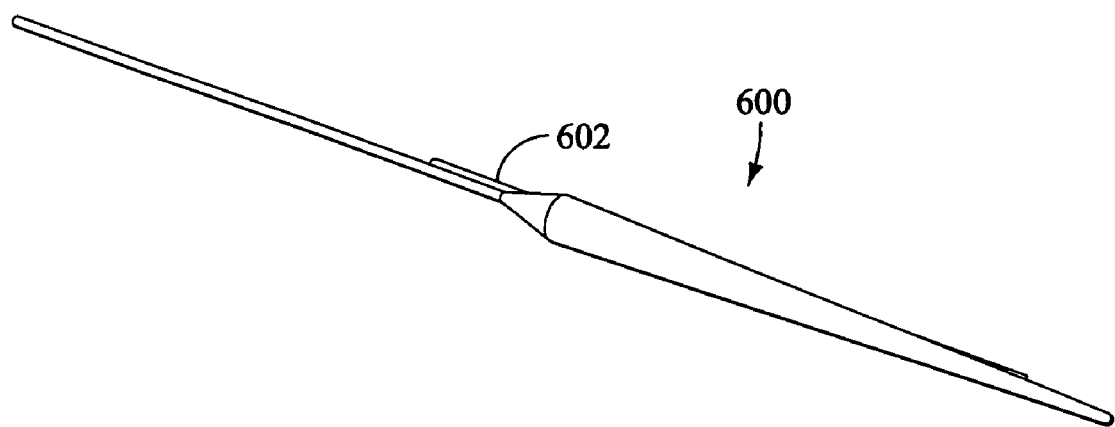
FIG. 17 shows a portion of a device used for deploying a branched vessel prosthesis.

A second introducer may be used to introduce the helical branched prosthesis 550 and create a tromboning connection. This second introducer may be based on the same principles as the introducer 500 described above, but could be less complex. For example, the second introducer may include a sheath for containing the branched prosthesis 550 in a compressed state, so that it can be introduced into a targeted anatomy and then released to either self-expand or be actively expanded with a balloon. The second introducer could be equipped with a delivery tip 600, as shown in FIG. 17, that allows for the deployment of a guide wire into the aortic bifurcation. A third introducer may be used to deploy the branch extension.

Deployment

Prosthetic modules are preferably deployed seriatim. The intermodular connection between the branched prosthesis 550 and the bifurcated prosthesis 520 is formed in situ. First the bifurcated prosthesis 520 is deployed, and then the branched prosthesis 550 is deployed. For example, a bifurcated aortic prosthesis 520, as described in WO98/53761, can be deployed into the abdominal aorta. The bifurcated prosthesis 520 has a generally inverted Y-shaped configuration having a body portion 523, a shorter leg 560 and a longer leg 532. The body of the prosthesis is constructed from tubular woven polyester fabric. At the proximal end of the prosthesis 520 is a self-expanding stent 521 which extends beyond the end of the prosthesis and has distally extending barbs 551. The shorter leg 560 and the longer leg 532 have internal projections extending from their distal termini.

This bifurcated prosthesis 520 can be deployed in any method known in the art, preferably the method described in WO98/53761 in which the devise is inserted by an introducer via a surgical cut-down into a femoral artery, and then advanced into the desired position over a stiff wire guide using endoluminal interventional techniques. For example, a guide wire (not shown) is first introduced into a femoral artery of the patient and advanced until its tip is beyond the desired deployment region of the prosthesis 520. At this stage, the introducer assembly 500 is fully assembled, and ready for introduction into the patient. The prosthesis 520 is retained at one end by the cylindrical sleeve 510 and the other by the distal attachment sections 540, and compressed by the sheath 530. If an aortic aneurism is to be repaired, the introducer assembly 500 can be inserted through a femoral artery over the guide wire, and positioned by radiographic techniques, which are not discussed here.

Once the introducer assembly 500 is in the desired deployment position, the sheath 530 is withdrawn to just proximal of the distal attachment section 540. This action releases the middle portion of the prosthesis 520 so that it can expand radially. The proximal self-expanding stent 521, however, is still retained within the cylindrical sleeve 510. Also, the distal end 542 of the prosthesis 520 is still retained within the external sheath 530.

Next, the pin vise 539 is released to allow small movements of the thin walled tube 515 with respect to the thick walled tube 541. These movements allow the prosthesis 520 to be lengthened or shortened or rotated or compressed for accurate placement in the desired location within the lumen. Radiopaque markers (not shown) may be placed along the prosthesis 520 to assist with placement of the prosthesis.

When the proximal end of the prosthesis 520 is in place, the proximal trigger wire is withdrawn by distal movement of the proximal wire release mechanism 524. The proximal wire release mechanism 524 and the proximal trigger wire can be completely removed by passing the proximal wire release mechanism 524 over the pin vise 539, the screw cap 546, and the connection means 516.

Next, the screw cap 546 of the pin vise 539 is then loosened. After this loosening, the thin walled tube 515 can be pushed in a proximal direction to move the cylindrical sleeve 510 in a proximal direction. When the cylindrical sleeve 510 no longer surrounds the self-expanding stent 521, the self-expanding stent 521 expands. When the self-expanding stent 521 expands, the barbs 551 grip the walls of the lumen to hold the proximal end of the prosthesis 520 in place. From this stage on, the proximal end of the prosthesis 520 cannot be moved again.

Once the proximal end of the prosthesis 520 is anchored, the external sheath 530 is withdrawn to distal of the distal attachment section 540. This withdrawal allows the contralateral limb 560 and the longer leg 532 of the prosthesis 520 to expand. At this point, the distal end 542 of the prosthesis 520 may still be moved. Consequently, the prosthesis 520 can still be rotated or lengthened or shortened for accurate positioning. Such positioning of the prosthesis 520 may ensure that the shorter leg 560 extends in the direction of a contralateral artery.

After the shorter leg 560 extends in the direction of the contra-iliac artery, the branched prosthesis 550 is deployed. The branched prosthesis 550 is deployed such that it forms a tromboning connection with the shorter leg 560 and extends from the shorter leg 560 into the contralateral artery. The coupling of the prosthesis 520 and branched prosthesis 550 is described in greater detail in other portions of this disclosure.

The method of introduction of the branched prosthetic module 550 is as follows. A guide wire (not shown) is introduced into the contralateral femoral artery and advanced until its tip is above the region into which the prosthesis is to be deployed. The second introducer is then advanced over the guide wire with an oscillating and rotating action until the extension prosthesis is overlapped one full stent within the contralateral limb 560. A final position check may then be made before the sheath is withdrawn while holding the thick walled tube in place.

The guide wire 602 can be deployed from the tip 600 of the second introducer captured and pulled over to the ipsilateral side to facilitate deployment of a third introducer through the ipsilateral side into the contralateral side to deploy a branch extension into the hypogastric artery. Preferably, a preloaded wire or snare within the limb of the prosthetic branch will preclude the need for complex localization, catheterization of branches and separate insertion of the wire through the sheath. This approach may be particularly important when multiple branches are present. The distal handle of the delivery system may be equipped with an additional trigger wire to accommodate this feature. The second and third introducers and the methods of using them are described in greater detail in U.S. Patent Application, "Introducer for an Iliac Side Branch Device," Ser. No. 60/510,823, filed Oct. 14, 2003, which is incorporated herein by reference.

The introducer and deployment method described above can be adapted for implantation in other regions. For example, if a first prosthetic module is placed into the aorta, a connecting prosthetic module can be placed into the renal, iliac, superior mesenteric, celiac or other artery to form a tromboning interconnection. If a first prosthetic module is placed into the thoracic aorta, a connecting prosthetic module can be placed into another portion of the thoracic aorta, the left subclavian, left common carotid, innominate or other artery. Furthermore, prosthetic modules which are implanted in the same artery can be connected to each other. The overlap region of each of these embodiments is preferably adapted to the size of the relevant anatomy and the forces to which the prostheses are exposed in the relevant anatomy.

EXAMPLE 1

The flow force on the branched limb is dependent upon the loads applied to the branch point and ultimate angulation of the prosthetic branch. Of particular interest are the forces that may cause separation of the branch extension from the prosthetic branch. Forces due to flow in the y-direction, if significant enough, can become larger than the frictional forces that hold the branch extension and the prosthetic branch together, resulting in separation. If the separation is substantial, a type III endoleak will occur and the aneurysm will no longer be excluded.

The prostheses described above may be subjected to an in vitro leak pressure test. The purpose of this test procedure is to determine the minimum internal pressure required causing leakage at the mating point between two prostheses.

The test requires a pressure transducer, a pressure monitor, water/glycerin mixture (dyed) @ 3.64cP, water bath, submersible heater, water pump, temperature controller, mating surface thermocouple, and mercury thermometer.

The prosthetic branch and branch extension are mated such that there is a suitable tromboning connection, preferably with a 1.5–2 cm overlap and a 1 mm or less difference in diameter at the interconnection. The devices may be ballooned for 30 seconds using a suitably sized balloon dilation catheter.

Internal pressure in the mated devices is measured utilizing a pressure transducer and pressure monitor. These instruments are connected to a syringe providing manually controlled pressure into the mated devices. The pressure liquid is a glycerin/water mixture to 3.64 centiPoise (cP) dyed with blue food coloring. The device was placed in a 37° C. water bath and the presence of a leak would be defined and identified by leakage of the blue-dyed glycerin/water mixture. Visual accounts of leakage and a recording of peak pressures were manually recorded.

EXAMPLE 2

The prostheses described above may be subjected to an in vivo test, preferably in non-human mammals. One animal that is suitable for implantation of the prosthesis for testing and therapeutic purposes is the domestic cow. For testing purposes, six- to ten-week-old male calves were used.

As presurgical preparation, each animal was given a daily dose of 325 mg of aspirin beginning on the day prior to the procedure for the purpose of platelet inhibition. Each animal was kept without food for approximately 8–12 hours and without water for approximately 2 hours preceding each procedure. A pre-operative baseline ACT was measured in a Hemochron Jr. Signature Series Machine (available from ITC in Edison, N.J.).

Each calf was sedated with Xylazine (1.0 mg/10 lbs, IM). Once the animal was lightly sedated, an induction mask was used to deliver Isofluorane (2–4%). The calf's face was placed into the mask while the inhalation anaesthetic was delivered. The animal may be intubated in standard fashion. Once the endotracheal tube was placed, it was secured. The ventilator was turned on and connected to the animal to increase the depth of anesthesia and mechanically ventilate the animals. Isofluorane dosages ranged from approximately 0.8–1.25%, although may be any percentage based on relevant factors. During this pre-surgical preparation, each animal may also receive an injection of benzathine procaine penicillin (30,000–50,000 U/kg IM).

The animal was placed on its left side with its right hind leg extended up and secured with gauze ties. A ground pad and EKG leads were placed on the animal. An intravenous catheter (IV) was placed in the peripheral leg vein and secured with tape. Lactate Ringers (LR) was infused through the catheter for the duration of the procedure to provide adequate hydration. Both groins were shaved and sterilely prepped with 70% alcohol and betadine.

The implantation of this branched vessel device involved basic endovascular techniques. A femoral cutdown was performed on the left leg to gain access to a femoral vessel. A retroperitoneal incision was performed to provide access to the right iliac artery. A third access point was gained via a cutdown exposing the right carotid artery. Hemostatic vessel loops were placed proximally and distally on the arteries. A single wall puncture needle was used to access the left femoral artery, and conformation of the cannulation was confirmed by the presence of pulsatile arterial flow from the needle hub.

Once the pulsatile flow was observed, a wire was placed in the descending abdominal aorta. The animal was heparinized with 200 IU of porcine heparin/kg. An activated clotting time was obtained within 3–10 minutes following heparin administration to ensure adequate anti-coagulation, to achieve a preferred minimum of 1.5–2 times the baseline ACT. An 8 French introducer sheath was advanced into the left arterial lumen. Before and after placement, the side port of each sheath was flushed with 0.9% normal saline.

A 5 French pigtail catheter was inserted over the wire through the introducer sheath and advanced into to the region of the aortic arch using fluoroscopic guidance. A baseline digital subtraction angiogram of the descending thoracic aorta was obtained utilizing an appropriate dose of contrast. Once the baseline angiogram had been achieved, a wire was placed through the pigtail catheter and advanced into the thoracic aorta. The catheter was then removed. A 12.5 MHz Boston Scientific IVUS (intravenous ultrasound) probe was inserted over the wire in a monorail fashion, and baseline IVUS measurements were obtained. These measurements included cross-sectional diameters of the distal abdominal aorta approximately 9 cm proximal to the trifurcation.

An external helical device similar to that shown in and described in reference to FIG. 11 was employed. This particular prosthesis was manufactured from a Viabahn® Endoprosthesis (W. L. Gore & Associates, Inc., Newark, Del.), which is made from expanded PTFE. It was loaded into an 18 French cartridge with a 4 French catheter providing 0.035 inch wire access through the man device and a preloaded 0.018 inch wire within the branched limb.

A single wall puncture needle was used to access the right iliac artery. Once an Amplatz guide wire was placed, a 20 French Check-Flo® (Cook, Inc., Bloomington, Ind.) introducer sheath was advanced to 9 cm above the aortic bifurcation and utilized as the delivery system. The preloaded 0.018 inch wire was advanced through the valve of the Check-Flo® sheath using a peal-away sheath. The loaded device cartridge was then inserted into the 20 French Check-Flo® using the dilators as pushers. The 0.018 inch wire was snared from the carotid artery to provide through-and-through access for the branch vessel wire. The prosthesis was then deployed to the point that the ostium of the prosthetic branch was exposed. The prosthesis was then advanced through the contralateral femoral artery.

The prosthesis was deployed with a 2.0 cm overlap within the prosthetic branch. The entire length of the prosthesis was ballooned with a 7 mm×4 cm balloon. Post implant angiographic and IVUS assessments were performed. The final IVUS assessment measured the proximal, mid and distal points of the stent graft along with the ostium, while the angiogram assessed the presence of any endoleaks, as well as the location of the stent graft. If desirable, the prosthesis may be explanted and subjected to post-explant analysis.

Throughout this specification various indications have been given as to the scope of the invention but the invention is not limited to any one of these but may reside at two more of these combined together. The examples are given for illustration only and not for limitation.

The invention claimed is:

1. An endoluminal prosthesis, comprising:
a prosthetic trunk comprising a trunk lumen extending therethrough, a wall, and an anastomosis in the wall, wherein the prosthetic trunk has a circumference; and
a prosthetic branch comprising a branch lumen extending therethrough, wherein the branch lumen is in fluid communication with the trunk lumen through the anastomosis, and wherein the prosthetic branch is disposed longitudinally along and circumferentially about the prosthetic trunk.

2. The prosthesis of claim 1, wherein the prosthetic branch extends about the prosthetic trunk at least about one-fourth the circumference of the prosthetic trunk.

3. The prosthesis of claim 2, wherein the prosthetic branch extends about the prosthetic trunk at least about one-half the circumference of the prosthetic trunk.

4. The prosthesis of claim 3, wherein the prosthetic branch extends about the prosthetic trunk at least about two-thirds the circumference of the prosthetic trunk.

5. The prosthesis of claim 3, wherein the prosthetic branch extends longitudinally along the prosthetic trunk more than about 10 mm.

6. The prosthesis of claim 5, wherein the prosthetic branch extends longitudinally along the prosthetic trunk more than about 30 mm.

7. The prosthesis of claim 6, wherein the prosthetic branch extends longitudinally along the prosthetic trunk more than about 50 mm.

8. The prosthesis of claim 6, further comprising a second prosthetic branch having a second branch lumen extending therethrough, wherein the second branch lumen is in fluid communication with the trunk lumen through a second anastomosis and wherein the second prosthetic branch is disposed longitudinally and circumferentially about the prosthetic trunk.

9. The prosthesis of claim 8, wherein both prosthetic branches shunt blood distally relative to the prosthetic trunk.

10. The prosthesis of claim 2, wherein the prosthetic branch has an angle of access that is greater than 20°.

11. The prosthesis of claim 10, wherein the angle of access is greater than 60°.

12. The prosthesis of claim 10, wherein the prosthetic branch is skewed between about 40° and about 60°.

13. The prosthesis of claim 2, wherein the prosthetic branch is skewed between about 0° and about 4°.

14. The prosthesis of claim 2, wherein the prosthetic branch has an angle of incidence that is between about 20° and about 60°.

15. The prosthesis of claim 14, wherein the prosthetic branch has an angle of incidence that is between about 35° and about 50°.

16. The prosthesis of claim 1, wherein the prosthetic branch extends longitudinally along the prosthetic trunk more than about 10 mm.

17. The prosthesis of claim 16, wherein the prosthetic branch extends longitudinally along the prosthetic trunk more than about 30 mm.

18. The prosthesis of claim 17, wherein the prosthetic branch extends longitudinally along the prosthetic trunk more than about 50 mm.

19. The prosthesis of claim 1, wherein the branch lumen is disposed longitudinally and circumferentially outside the prosthetic trunk.

20. The prosthesis of claim 1, wherein the branch lumen is disposed longitudinally and circumferentially inside the prosthetic trunk.

21. The prosthesis of claim 1, wherein the prosthetic branch is attached at a point on the prosthetic trunk that is distal to the anastomosis.

22. The prosthesis of claim 21, wherein the prosthetic branch is attached at multiple points on the prosthetic trunk that are distal to the anastomosis.

23. The prosthesis of claim 1, wherein the prosthetic branch is attached at a point on the prosthetic trunk that is proximal to the anastomosis.

24. The prosthesis of claim 23, wherein the prosthetic branch is attached at multiple points on the prosthetic trunk that are proximal to the anastomosis.

25. The prosthesis of claim 1, wherein the prosthetic branch comprises a proximal ostium and a distal ostium.

26. The prosthesis of claim 25, wherein the proximal ostium is infundibular.

27. The prosthesis of claim 25, wherein the diameter of the proximal ostium of the prosthetic branch is larger than the distal ostium of the prosthetic branch.

28. The prosthesis of claim 25, wherein the distal ostium is beveled.

29. The prosthesis of claim 1, further comprising a second prosthetic branch having a second branch lumen extending therethrough, wherein the second branch lumen is in fluid communication with the trunk lumen through a second anastomosis and wherein the second prosthetic branch is disposed longitudinally and circumferentially about the prosthetic trunk.

30. The prosthesis of claim 1, further comprising a branch extension connected to and in fluid communication with the prosthetic branch.

31. A method of connecting modules of an endoluminal prosthesis, comprising:
 providing a prosthetic trunk;
 providing a prosthetic branch having proximal and distal ends;
 anastomosing the proximal end of the prosthetic branch to the prosthetic trunk; and
 positioning the prosthetic branch and attaching the prosthetic branch to the prosthetic trunk so as to provide a fluid passage in a helical direction.

32. A method of increasing the angle of access for an endoluminal prosthesis, comprising:
 providing a prosthetic trunk comprising a trunk lumen extending therethrough, a wall and an anastomosis in the wall; and
 providing a prosthetic branch having a branch lumen extending therethrough, wherein the branch lumen is in fluid communication with the trunk lumen through the anastomosis and disposed longitudinally and circumferentially about the trunk lumen.

* * * * *

UNITED STATES PATENT AND TRADEMARK OFFICE
CERTIFICATE OF CORRECTION

PATENT NO.      : 7,105,020 B2
APPLICATION NO. : 10/756803
DATED           : September 12, 2006
INVENTOR(S)     : Roy K. Greenberg et al.

It is certified that error appears in the above-identified patent and that said Letters Patent is hereby corrected as shown below:

In the Claims

Column 22, in claim 12, line 1, after "prosthesis of" delete "claim 10" and substitute --claim 2-- in its place.

Signed and Sealed this

Fourth Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,105,020 B2 Page 1 of 1
APPLICATION NO. : 10/756803
DATED : September 12, 2006
INVENTOR(S) : Roy K. Greenberg et al.

It is certified that error appears in the above-identified patent and that said Letters Patent is hereby corrected as shown below:

Column 22, in claim 13, line 2, after "and about" delete "4°" and substitute --40°-- in its place.

Signed and Sealed this

Fifteenth Day of April, 2008

JON W. DUDAS
*Director of the United States Patent and Trademark Office*